(12) United States Patent
Kanai et al.

(10) Patent No.: US 9,067,923 B2
(45) Date of Patent: Jun. 30, 2015

(54) SUBSTITUTED QUINOXALINES

(71) Applicant: Kyowa Hakko Kirin Co., Ltd., Tokyo (JP)

(72) Inventors: Toshimi Kanai, Tokyo (JP); Kenji Uchida, Tokyo (JP); Masakazu Honma, Tokyo (JP); Yuichi Fukuda, Tokyo (JP)

(73) Assignee: KYOWA HAKKO KIRIN CO., LTD., Tokyo (JP)

( * ) Notice: Subject to any disclaimer, the term of this patent is extended or adjusted under 35 U.S.C. 154(b) by 0 days.

(21) Appl. No.: 14/356,220

(22) PCT Filed: Nov. 9, 2012

(86) PCT No.: PCT/JP2012/079109
§ 371 (c)(1),
(2) Date: May 5, 2014

(87) PCT Pub. No.: WO2013/069765
PCT Pub. Date: May 16, 2013

(65) Prior Publication Data
US 2014/0309231 A1    Oct. 16, 2014

(30) Foreign Application Priority Data
Nov. 9, 2011   (JP) ................................ 2011-245388

(51) Int. Cl.
| | | |
|---|---|---|
| *C07D 241/44* | (2006.01) | |
| *C07D 401/14* | (2006.01) | |
| *C07D 413/14* | (2006.01) | |
| *C07D 417/12* | (2006.01) | |
| *C07D 417/14* | (2006.01) | |
| *A61K 9/00* | (2006.01) | |
| *A61K 47/02* | (2006.01) | |
| *A61K 47/26* | (2006.01) | |
| *A61K 9/20* | (2006.01) | |
| *A61K 9/48* | (2006.01) | |

(52) U.S. Cl.
CPC ............ *C07D 401/14* (2013.01); *C07D 413/14* (2013.01); *C07D 417/12* (2013.01); *C07D 417/14* (2013.01); *A61K 9/0019* (2013.01); *A61K 47/02* (2013.01); *A61K 47/26* (2013.01); *A61K 9/2018* (2013.01); *A61K 9/2054* (2013.01); *A61K 9/2059* (2013.01); *A61K 9/4866* (2013.01)

(58) Field of Classification Search
CPC .................................................. C07D 241/44
USPC ........ 544/356, 405; 546/199, 268.1; 548/131, 548/202, 235
See application file for complete search history.

(56) References Cited

U.S. PATENT DOCUMENTS

| | | |
|---|---|---|
| 6,083,951 A | 7/2000 | Bradbury |
| 2007/0093491 A1 | 4/2007 | Baxter et al. |
| 2009/0042868 A1 | 2/2009 | Andersen et al. |
| 2011/0237584 A1* | 9/2011 | Amishiro et al. .......... 514/234.8 |
| 2012/0058079 A1 | 3/2012 | Combs et al. |
| 2013/0065905 A1 | 3/2013 | Fukuda et al. |

FOREIGN PATENT DOCUMENTS

| | | |
|---|---|---|
| JP | 9-510987 | 11/1997 |
| JP | 2006-137723 | 6/2006 |
| JP | 2007-503432 | 2/2007 |
| JP | 2008-505937 | 2/2008 |
| JP | 2008-201756 | 9/2008 |
| JP | 2011-527686 | 11/2011 |
| WO | 97/32858 | 9/1997 |
| WO | 00/42026 | 7/2000 |
| WO | 03/051870 | 6/2003 |

(Continued)

OTHER PUBLICATIONS

Jordan, V. C. Nature Reviews: Drug Discovery, 2, 2003, 205.*
Hackam, et al. JAMA, 296(14), 2006, 1731-1732.*
International Search Report issued Jan. 15, 2013 in International (PCT) Application No. PCT/JP2012/079109.
R. H. Bradbury et al., "New Non-Peptide Endothelin-A Receptor Antagonists: Synthesis, Biological Properties, and Structure-Activity Relationships of 5-(Dimethylamino)-*N*-pyridyl-, -*N*-pyrimidinyl-, -*N*-pyridazinyl-, and -*N*-pyrazinyl-1-naphthalenesulfonamides", Journal of Medicinal Chemistry, vol. 40, pp. 996-1004, 1997.

*Primary Examiner* — Douglas M Willis
(74) *Attorney, Agent, or Firm* — Wenderoth, Lind & Ponack, L.L.P.

(57) ABSTRACT

A nitrogen-containing heterocyclic compound represented by formula (I-A):

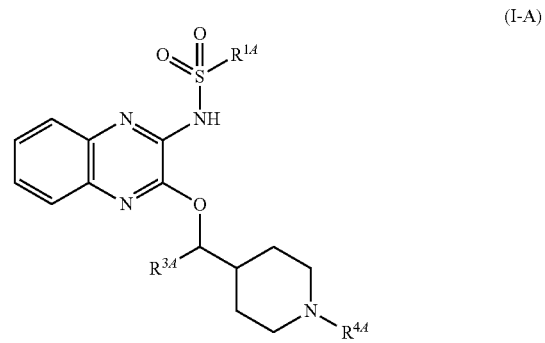

(wherein
R$^{1A}$ represents lower alkyl which may be substituted with lower alkoxy,
R$^{3A}$ represents lower alkyl substituted with fluorine atom (s), and
R$^{4A}$ represents an optionally substituted aromatic heterocyclic group) or the like, or a pharmaceutically acceptable salt thereof; and the like, are provided.

4 Claims, 1 Drawing Sheet

(56) References Cited

FOREIGN PATENT DOCUMENTS

| | | |
|---|---|---|
| WO | 03/059893 | 7/2003 |
| WO | 2004/007472 | 1/2004 |
| WO | 2005/021513 | 3/2005 |
| WO | 2005/023771 | 3/2005 |
| WO | 2007-023186 | 3/2007 |
| WO | 2007/044729 | 4/2007 |
| WO | 2010/053182 | 5/2010 |
| WO | 2011/142316 | 11/2011 |

* cited by examiner

SUBSTITUTED QUINOXALINES

TECHNICAL FIELD

The present invention relates to a nitrogen-containing heterocyclic compound having an inhibitory effect on the production of kynurenine or a pharmaceutically acceptable salt thereof; a kynurenine production inhibitor comprising one or more of said compounds and/or salts thereof as an active ingredient; and the like.

BACKGROUND OF THE INVENTION

Cancer cells excessively express tumor-associated antigens. The host immune system is considered to respond to the tumor-associated antigens and exert cellular immunity to eliminate the tumor. However, there exist various types of immune escape mechanisms in the tumor micro-environment or throughout the body, and when the host fails to eliminate the tumor, the tumor grows.

Recently it has been reported that indoleamine 2,3-dioxygenase (IDO), which is a tryptophan-metabolizing enzyme, inhibits the proliferation of T cells and NK cells and activates regulatory T cells, thereby causing the depression of the host immune system. The expression of IDO is increased in tumor tissues and induced by IFN-γ stimulation in cancer cells and dendritic cells (for example, J. Clin. Invest., vol. 117, No. 5, pp. 1147-1154 (2007)). In a human body, 90% of tryptophan, which is the essential amino acid, is metabolized into kynurenine and subsequently into 3OH-kynurenine, quinolinic acid, and the like in the kynurenine pathway, whose initiation step involves IDO. Activation of IDO decreases the tryptophan concentration and increases the kynurenine concentration in a local or systemic manner, and the tryptophan metabolites including kynurenine induce the death of T cells and NK cells (for example, J. Exp. Med., vol. 196, No. 4, pp. 447-457 (2002)). The tryptophan metabolism also induces the conversion of CD4$^+$CD25$^-$ T cells into regulatory T cells (for example, Blood, vol. 109, No. 7, pp. 2871-2877 (2007)). In the culture supernatant of dendritic cells in which the expression of IDO is induced by INF-γ, the tryptophan concentration is decreased and the kynurenine concentration is increased. When T cells are co-cultured with such dendritic cells, T cell proliferation is suppressed compared to co-culture with unstimulated dendritic cells (for example, J. Exp. Med., vol. 196, No. 4, pp. 447-457 (2002)).

As described above, in the tumor environment with an increased expression of IDO, an increased kynurenine concentration induced by tryptophan metabolism suppresses antitumor effector cells, which is considered to be one of the immune escape mechanisms in tumors (for example, J. Clin. Invest., vol. 117, No. 5, pp. 1147-1154 (2007)).

An increased expression of IDO in the tumor tissues of colorectal cancer and prostate cancer has been reported (for example, Clin. Cancer Res., vol. 12, No. 4, pp. 1144-1151 (2006); and Eur. J. Cancer, vol. 44, No. 15, pp. 2266-2275 (2008)). In acute myeloid leukemia cells, IDO is constantly expressed (for example, Leukemia, vol. 21, pp. 353-355 (2007)). It has also been reported that when patients with endometrial cancer, melanoma or ovarian cancer has an increased expression of IDO, the patients will have a poor prognosis (for example, Br. J. Cancer, vol. 95, No. 11, pp. 1555-1561 (2006); J. Clin. Invest., vol. 114, No. 2, pp. 280-290 (2004); and Clin. Cancer Res., vol. 11, No. 16, pp. 6030-6039 (2005)). In adult T cell leukemia lymphoma and acute myeloid leukemia, the kynurenine/tryptophan ratio in the blood is increased (for example, Leuk. Res., vol. 33, No. 1, pp. 39-45 (2009); and Leuk. Res., vol. 33, No. 3, pp. 490-494 (2009)). It has also been reported that melanoma patients with an increased kynurenine/tryptophan ratio in the blood will have a poor prognosis (for example, Dermatology, vol. 214, No. 1, pp. 8-14 (2007)). As described above, IDO and/or kynurenine is considered to be involved in various types of solid cancers and hematologic cancers.

1-methyltryptophan (1-MT), which is a tryptophan derivative, antagonizes tryptophan, thereby inhibiting the production of kynurenine (for example, Cancer Res., vol. 67, No. 2, pp. 702-300 (2007)). 1-MT cancels the suppression of T cell proliferation in the presence of IDO-expressing cancer cells or IDO-expressing dendritic cells (for example, Cancer Res., vol. 67, No. 2, pp. 792-800 (2007)). Further, 1-MT induces major histocompatibility complex (MHC)-restricted rejection in allogeneic pregnant mice (for example, Nat. Immunol., vol. 2, No. 1, pp. 64-68 (2001)). These results suggest that inhibition of IDO suppresses the production of kynurenine and induces immunity.

1-MT shows an antitumor effect in tumor-bearing mice with mouse melanoma cells. This effect disappears in immunodeficient mice (for example, Cancer Res., vol. 67, No. 2, pp. 792-800 (2007)). These results suggest that the antitumor effect of 1-MT is based on immunostimulation by IDO inhibition-mediated inhibitory effect on the production of kynurenine.

In addition, compounds showing an inhibitory effect on the production of kynurenine and/or on IDO are known to exhibit an immunostimulatory effect (for example, Nat. Immunol., vol. 2, pp. 64-68 (2001)).

On the other hand, it has been reported that the IDO expression in PBMC correlates with the viral load in HIV positive patients (for example, Blood, vol. 109, pp. 3351-3359 (2007)). It has also been reported that chronic hepatitis C patients have an increased IDO mRNA level in the liver and an increased serum kynurenine/tryptophan ratio (for example, J Virol., vol. 81, No. 7, pp. 3662-3666 (2007)).

Further, compounds showing an inhibitory effect on the production of kynurenine and/or on IDO are known to be useful as an antitumor agent, an anti-AIDS agent, an anti-AIDS dementia agent, an anti-Alzheimer's disease agent, an antidepressant, or the like (for example, J Clin Invest., vol. 117, pp. 1147-1154 (2007); J Virol., vol. 81, pp. 11593-11603 (2007); Neuropathol Appl Neurobiol., vol. 31, pp. 395-404 (2005); Neurosci Lett., vol. 187, pp. 9-12 (1995); and Neuropsychopharmacology, vol. 33, pp. 2341-2351 (2008)).

As described above, IDO inhibitors and/or kynurenine production inhibitors are considered to foe promising preventive or therapeutic agents for diseases associated with the production of kynurenine, such as cancers, AIDS, AIDS dementia, Alzheimer's disease, depression, infections, and immune diseases.

On the other hand, pyrazine derivatives having an antagonistic effect on endothelin are known (see Patent Literature 1 and Non Patent literature 1).

Compounds known as a therapeutic agent for diseases in which chemokines are involved are N-pyrazinyl-2-thiophenesulfonamide derivatives (see Patent Literature 2), N-pyrazinylbenzenesulfonamide derivatives (see Patent Literature 3), N-(2-quinoxalinyl)benzenesulfonamide derivatives (see Patent Literature 4), and the like. Compounds known as a chemokine receptor antagonist are N-pyrazinylbenzenesulfonamide derivatives, N-(2-quinoxalinyl)benzenesulfonamide derivatives (see Patent Literature 5 and 6), pyridopyrazin-2-on-3-ylmethanesulfonamide derivatives (see Patent Literature 7), and the like. Compounds known as a functional modulator of thymus and activation-regulated chemokine (TARC; CC cherookine ligand 17 (CCL17)) and/or of macrophage-derived chemokine (MDC: CC chemokine ligand 22 (CCL22)) are N-pyrazinylbenzenesulfonamide derivatives, N-(2-pyridopyrazinyl)benzenesulfonamide derivatives (see Patent Literature 8), and the like.

N-(2-quinoxalinyl)benzenesulfonamide derivatives having an inhibitory activity on phosphatidylinositol-3-kinase (PI3K) (see Patent Literatures 9 and 10), and the like, are known.

Also, a nitrogen-containing heterocyclic compound having an inhibitory effect on the production of kynurenine (see Patent Literature 11) is known.

Further, 2,3-disubstituted quinoxaline derivatives having GLP-1 agonist activity (see Patent Literature 12) are known.

PRIOR ART LITERATURE

Patent Literature

Patent Literature 1: JP 9-510987 T
Patent Literature 2: WO 03/051870
Patent Literature 3: WO 03/059893
Patent Literature 4: WO 05/021513
Patent Literature 5: WO 04/007472
Patent Literature 6: WO 05/023771
Patent Literature 7: WO 97/032858
Patent Literature 6: JP 2006-137723 A
Patent Literature 9: WO 07/044729
Patent Literature 10: WO 07/023186
Patent Literature 11: WO 2010/053182
Patent Literature 12: WO 2000/042026

Non Patent Literature

Non Patent Literature 1: Journal of Medicinal Chemistry, 1997, vol. 40, p. 996

SUMMARY OF INVENTION

Problems to be Solved by Invention

An object of the present invention is to provide a nitrogen-containing heterocyclic compound having an inhibitory effect on the production of kynurenine or a pharmaceutically acceptable salt thereof; a kynurenine production inhibitor comprising one or more of said compounds and/or salts thereof as an active ingredient; and the like.

Means for Solving the Problems

The present invention relates to the following (1) to (21).
(1) A nitrogen-containing heterocyclic compound represented by formula (I):

[Chemical Formula 1]

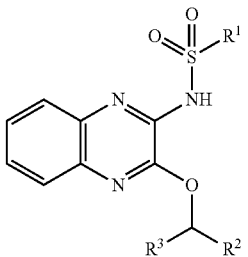

(I)

(wherein
$R^1$ represents lower alkyl which may be substituted with lower alkoxy,
$R^2$ represents formula (II):

[Chemical Formula 2]

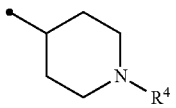

(II)

(wherein $R^4$ represents an optionally substituted aromatic heterocyclic group),
formula (III):

[Chemical Formula 3]

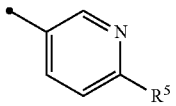

(III)

[wherein $R^5$ represents formula (III-1):

[Chemical Formula 4]

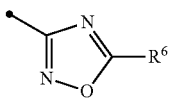

(III-1)

(wherein $R^6$ represents lower alkyl which may be substituted with lower alkoxy, or cycloalkyl) or oxazol-5-yl], or
formula (IV):

[Chemical Formula 5]

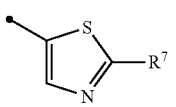

(IV)

(wherein $R^7$ represents lower alkanoyl), and
$R^3$ represents lower alkyl substituted with fluorine atom(s)} or a pharmaceutically acceptable salt thereof.

(2) The nitrogen-containing heterocyclic compound or a pharmaceutically acceptable salt thereof according to (1), wherein $R^2$ represents formula (II).

(3) The nitrogen-containing heterocyclic compound or a pharmaceutically acceptable salt thereof according to (1), wherein $R^2$ represents formula (II-A):

[Chemical Formula 6]

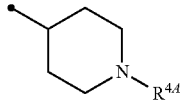
(II-A)

(wherein $R^{4A}$ represents optionally substituted pyridyl, optionally substituted, tetrazolyl, optionally substituted pyrazinyl, optionally substituted pyrimidinyl, or optionally substituted thiazolyl).

(4) The nitrogen-containing heterocyclic compound or a pharmaceutically acceptable salt thereof according to (1), wherein $R^2$ represents formula (XII-A):

[Chemical Formula 7]

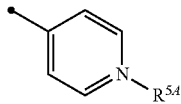
(III-A)

[wherein $R^{5A}$ represents formula (III-1-A):

[Chemical Formula 8]

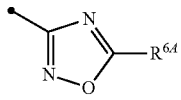
(III-1-A)

(wherein $R^{6A}$ represents lower alkyl substituted with lower alkoxy, or cycloalkyl)].

(5) The nitrogen-containing heterocyclic compound or a pharmaceutically acceptable salt thereof according to (1), wherein the moiety represented by

[Chemical Formula 9]

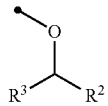

in formula (I) represents

[Chemical Formula 10]

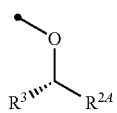

[wherein
$R^{2A}$ represents formula (III-B):

[Chemical Formula 11]

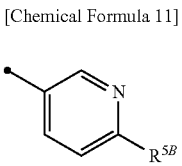
(III-B)

[wherein $R^{5B}$ represents formula (III-1-B):

[Chemical Formula 12]

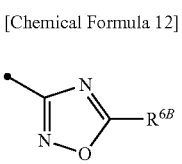
(III-1-B)

(wherein $R^{6B}$ represents lower alkyl or cycloalkyl) or oxazol-5-yl] or
formula (IV):

[Chemical Formula 13]

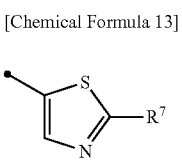
(IV)

(wherein $R^7$ has the same meaning as defined above), and $R^8$ has the same meaning as defined above).

(6) The nitrogen-containing heterocyclic compound or a pharmaceutically acceptable salt thereof according to (5), wherein $R^{2A}$ represents formula (III-B).

(7) The nitrogen-containing heterocyclic compound or a pharmaceutically acceptable salt thereof according to (5), wherein $R^{2A}$ represents formula (IV).

(8) The nitrogen-containing heterocyclic compound or a pharmaceutically acceptable salt thereof according to any of (1) to (7), wherein $R^3$ represents trifluoromethyl.

(9) The nitrogen-containing heterocyclic compound or a pharmaceutically acceptable salt thereof according to (1), wherein the nitrogen-containing heterocyclic compound is selected from the following compound group:
N-dimethyl-2-(4-(2,2,2-trifluoro-1-(3-(propylsulfonamido) quinoxalin-2-yloxy)ethyl)piperidin-1-yl)isonicatinamide (compound 1),
N,N-dimethyl-2-(4-(2,2,2-trifluoro-1-(3-(propylsulfonamido) quinoxalin-2-yloxy)ethyl)piperidin-1-yl)nicotinamide (compound 2),
N,N-dimethyl-6-(4-(2,2,2-trifluoro-1-(3-(propylsulfonamido) quinoxalin-2-yloxy)ethyl)piperidin-1-yl)picolinamide (compound 3),
N-(3-(1-(1-(6-cyanopyridin-3-yl)piperidin-4-yl)-2,2,2-trifluoroethoxy)quinoxalin-2-yl)propane-1-sulfonamide (compound 4),
5-(4-(2,2,2-trifluoro-1-(3-(propylsulfonamido)quinoxalin-2-yloxy)ethyl)piperidin-1-yl)picolinamide (compound 5),
N-(3-(1-(1-(4-cyanopyridin-2-yl)piperidin-4-yl)-2,2,2-trifluoroethoxy)quinoxalin-2-yl)propane-1-sulfonamide (compound 6),
N-(3-(1-(1-(5-cyanopyridin-3-yl)piperidin-4-yl)-2,2,2-trifluoroethoxy)quinoxalin-2-yl)propane-1-sulfonamide (compound 7), N,N-dimethyl-6-(4-(2,2,2-trifluoro-1-(3-(propylsulfonamido) quinoxalin-2-yloxy)ethyl)piperidin-1-yl)nicotinamide (compound 8),
N-(3-(1-(1-(3-cyanopyridin-2-yl)piperidin-4-yl)-2,2,2-trifluoroethoxy)quinoxalin-2-yl)propane-1-sulfonamide (compound 9),
2-(4-(2,2,2-trifluoro-1-(3-(propylsulfonamido)quinoxalin-2-yloxy)ethyl)piperidin-1-yl)nicotinamide (compound 10),
N-(3-(2,2,2-trifluoro-1-(1-(2-methyl-2H-tetrazol-5-yl) piperidin-4-yl)ethoxy)quinoxalin-2-yl)propane-1-sulfonamide (compound 11),
N-(3-(2,2,2-trifluoro-1-(1-(1-methyl-1H-tetrazol-5-yl) piperidin-4-yl)ethoxy)quinoxalin-2-yl)propane-1-sulfonamide (compound 12),
N-(3-(2,2,2-trifluoro-1-(1-(pyrazin-2-yl)piperidin-4-yl) ethoxy)quinoxalin-2-yl)propane-1-sulfonamide (compound 13),
N-(3-(2,2,2-trifluoro-1-(1-(pyrimidin-5-yl)piperidin-4-yl) ethoxy)quinoxalin-2-yl)propane-1-sulfonamide (compound 14),
N-(3-(1-(1-(5-cyanopyridin-2-yl)piperidin-4-yl)-2,2,2-trifluoroethoxy)quinoxalin-2-yl)propane-1-sulfonamide (compound 15),
N-(3-(1-(1-(2-cyanopyridin-4-yl)piperidin-4-yl)-2,2,2-trifluoroethoxy)quinoxalin-2-yl)propane-1-sulfonamide (compound 16),
N-(3-(1-(1-(3-cyanopyridin-4-yl)piperidin-4-yl)-2,2,2-trifluoroethoxy)quinoxalin-2-yl)propane-1-sulfonamide (compound 17),
N-(3-(2,2,2-trifluoro-1-(1-(thiazol-2-yl)piperidin-4-yl) ethoxy)quinoxalin-2-yl)propane-1-sulfonamide (compound 18),
6-(4-(2,2,2-trifluoro-1-(3-(propylsulfonamide)quinoxalin-2-yloxy)ethyl)piperidin-1-yl)nicotinamide (compound 19),
N-(3-(2,2,2-trifluoro-1-(1-(pyridin-2-yl)piperidin-4-yl) ethoxy)quinoxalin-2-yl)propane-1-sulfonamide (compound 20),
N-(3-(2,2,2-trifluoro-1-(1-(pyridin-3-yl)piperidin-4-yl) ethoxy)quinoxalin-2-yl)propane-1-sulfonamide (compound 21), and
N-(3-(2,2,2-trifluoro-1-(1-(pyridin-4-yl)piperidin-4-yl) ethoxy)quinoxalin-2-yl)propane-1-sulfonamide (compound 22).

(10) The nitrogen-containing heterocyclic compound or a pharmaceutically acceptable salt thereof according to (1), wherein the nitrogen-containing heterocyclic compound is selected from the following compound group:
N-(3-(1-(6-(5-cyclopropyl-1,2,4-oxadiazol-3-yl)pyridin-3-yl)-2,2,2-trifluoroethoxy)quinoxalin-2-yl)-2-methoxyethanesulfonamide (compound 23),
2-methoxy-N-(3-(2,2,2-trifluoro-1-(6-(5-(methoxymethyl)-1,2,4-oxadiasol-3-yl)pyridin-3-yl)ethoxy)quinoxalin-2-yl) ethanesulfonamide (compound 24),
N-(3-(1-(6-(5-cyclopropyl-1,2,4-oxadiazol-3-yl)pyridin-3-yl)-2,2,2-trifluoroethoxy)quinoxalin-2-yl)propane-1-sulfonamide (compound 25),
N-(3-(2,2,2-trifluoro-1-(6-(5-(methoxymethyl)-1,2,4-oxadiazol-3-yl)pyridin-3-yl)ethoxy)quinoxalin-2-yl)propane-1-sulfonamide (compound 26), and
2-methoxy-N-(3-(2,2,2-trifluoro-1-(6-(5-methyl-1,2,4-oxadiazol-3-yl)pyridin-3-yl)ethoxy)quinoxalin-2-yl) ethanesulfonamide (compound 27).

(11) The nitrogen-containing heterocyclic compound or a pharmaceutically acceptable salt thereof according to (1), wherein the nitrogen-containing heterocyclic compound is selected from the following compound group:
(R)-N-(3-(2,2,2-trifluoro-1-(6-(5-methyl-1,2,4-oxadiazol-3-yl)pyridin-3-yl)ethoxy)quinoxalin-2-yl)propane-1-sulfonamide (compound 28),
(R)-2-methoxy-N-(3-(2,2,2-trifluoro-1-(6-(oxazol-5-yl) pyridin-3-yl)ethoxy)quinoxalin-2-yl)ethanesulfonamide (compound 30),
(S)-N-(3-(1-(2-acetylthiazol-5-yl)-2,2,2-trifluoroethoxy) quinoxalin-2-yl)propane-1-sulfonamide (compound 32),
(R)-5-(4-2,2,2-trifluoro-1-(3-(propylsulfonamido) quinoxalin-2-yloxy)ethyl)piperidin-1-yl)picolinamide (compound 34), and
(R)-N-(3-(1-(6-(5-cyclopropyl-1,2,4-oxadiazol-3-yl)pyridin-3-yl)-2,2,2-trifluoroethoxy)quinoxalin-2-yl)-2-methoxyethanesulfonamide (compound 37).

(12) The nitrogen-containing heterocyclic compound or a pharmaceutically acceptable salt thereof according to (1), wherein the nitrogen-containing heterocyclic compound is selected from the following compound group:
(S)-N-(3-(2,2,2-trifluoro-1-(6-(5-diethyl-1,2,4-oxadiazol-3-yl)pyridin-3-yl)ethoxy)quinoxalin-2-yl)propane-1-sulfonamide (compound 29),
(S)-2-methoxy-N-(3-(2,2,2-trifluoro-1-(6-(oxazol-5-yl)pyridin-3-yl)ethoxy)quinoxalin-2-yl)ethanesulfonamide (compound 31),
(R)-N-(3-(1-(2-acetylthiazol-5-yl)-2,2,2-trifluoroethoxy) quinoxalin-2-yl)propane-1-sulfonamide (compound 33),
(S)-5-(4-(2,2,2-trifluoro-1-(3-(propylsulfonamido) quinoxalin-2-yloxy)ethyl)piperidin-1-yl)picolinamide (compound 35), and
(S)-N-(3-(1-(6-(S-cyclopropyl-1,2,4-oxadiazol-3-yl)pyridin-3-yl)-2,2,2-trifluoroethoxy)quinoxalin-2-yl)-2-methoxyethanesulfonamide (compound 36).

(13) A medicament comprising, as an active ingredient, the nitrogen-containing heterocyclic compound described in any of (1) to (12) or a pharmaceutically acceptable salt thereof.

(14) A kynurenine production inhibitor comprising, as an active ingredient, the nitrogen-containing heterocyclic compound described in any of (1) to (12) or a pharmaceutically acceptable salt thereof.

(15) A method for inhibiting the production of kynurenine, comprising a step of administering an effective amount of the nitrogen-containing heterocyclic compound described in any of (1) to (12) or a pharmaceutically acceptable salt thereof.

(16) Use of the nitrogen-containing heterocyclic compound described in any of (1) to (12) or a pharmaceutically acceptable salt thereof for the manufacture of a kynurenine production inhibitor.

(17) The nitrogen-containing heterocyclic compound described in any of (1) to (12) or a pharmaceutically acceptable salt thereof for use in the inhibition of the production of kynurenine.

(18) A preventive or therapeutic agent for a disease associated with the production of kynurenine, comprising, as an active ingredient, the nitrogen-containing heterocyclic compound described in any of (1) to (12) or a pharmaceutically acceptable salt thereof.

(19) A method for preventing or treating a disease associated with the production of kynurenine, comprising a step of administering an effective amount of the nitrogen-containing heterocyclic compound described in any of (1) to (12) or a pharmaceutically acceptable salt thereof.

(20) Use of the nitrogen-containing heterocyclic compound described in any of (1) to (12) or a pharmaceutically acceptable salt thereof for the manufacture of a preventive or therapeutic agent for a disease associated with the production of kynurenine.

(21) The nitrogen-containing heterocyclic compound described in any of (1) to (12) or a pharmaceutically acceptable salt thereof for use in the prevention or treatment of a disease associated with the production of kynurenine.

Effects of Invention

The present invention provides a nitrogen-containing heterocyclic compound having an inhibitory effect on the production of kynurenine or a pharmaceutically acceptable salt thereof; a kynurenine production inhibitor comprising one or more of said compounds and/or salts thereof as an active ingredient; and the like.

DETAILED DESCRIPTION OF THE INVENTION

Figure 1:
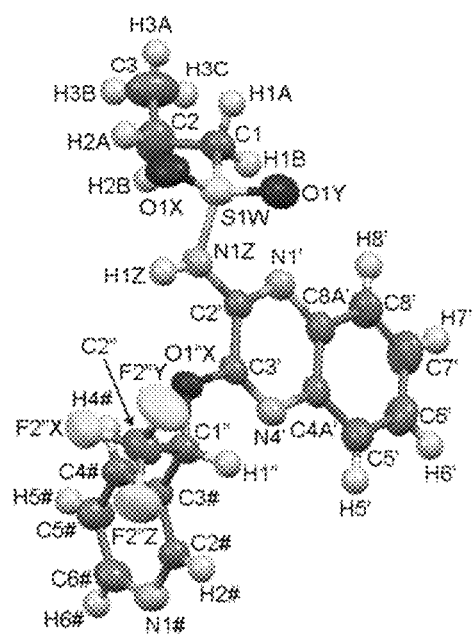
FIG. 1 shows the molecular structure of compound 312 (WO 2010/053182) in a crystal. Non-hydrogen atoms are drawn as 50% probability ellipsoids and hydrogen atoms are drawn as spheres of arbitrary radii.

Hereinafter, the compound represented by the above formula (I) is referred to as compound (I). The same applies to the other compounds having different formula numbers.

In the definition of each group is the formula (I);
(i) Examples of the lower alkyl and the lower alkyl moieties of the lower alkanoyl and the lower alkoxy include linear or branched alkyl having 1 to 10 carbon atoms, more specifically, methyl, ethyl, n-propyl, isopropyl, n-butyl, isobutyl, sec-butyl, tert-butyl, n-pentyl, neopentyl, n-hexyl, n-heptyl, n-octyl, n-nonyl, n-decyl, and the like.
(ii) Examples of the lower alkyl substituted with fluorine atom(s) include a lower alkyl substituted with from one up to the maximum possible number of fluorine atoms, more specifically, difluoromethyl, trifluoromethyl, (1-fluoro-1-methyl)ethyl, 1,1,2,2,2-pentafluoroethyl, and the like.
(iii) Examples of the cycloalkyl include cycloalkyl having 3 to 10 carbon atoms, more specifically, cyclopropyl, cyclobutyl, cyclopentyl, cyclohexyl, cycloheptyl, cyclooctyl, cyclononyl, cyclodecyl, and the like.
(iv) Examples of the aromatic heterocyclic group include a 5- or 6-membered monocyclic aromatic heterocyclic group containing at least one heteroatom selected from a nitrogen atom, an oxygen atom and a sulfur atom; a bicyclic or tricyclic aromatic heterocyclic group in which 3- to 8-membered rings are fused and which contains at least one heteroatom selected from a nitrogen atom, an oxygen atom and a sulfur atom; a fused tricyclic aromatic heterocyclic group in which 3- to 8-membered rings are fused and which contains at least one heteroatom selected from a nitrogen atom, an oxygen atom and a sulfur atom; and the like, more specifically, furyl, thienyl, pyrrolyl, imidazolyl, pyrazolyl, oxazolyl, isoxazolyl, oxadiazolyl, thiazolyl, isothiazolyl, thiadiazolyl, triazolyl, tetrazolyl, pyridyl, pyridyl-1-oxide, pyridazinyl, pyrimidinyl, pyrazinyl, triazinyl, benzofuranyl, benzothiophenyl, benzoxazolyl, benzothiazolyl, isoindolyl, indolyl, indazolyl, benzimidazolyl, benzotriazolyl, oxazolopyrimidinyl, thiazolopyrimidinyl, pyrrolopyridinyl, pyrrolopyrimidinyl, imidazopyridyl, purinyl, guinolinyl, isoquinolinyl, cinnolinyl, phthalazinyl, quinazolinyl, quinoxalinyl, naphthyridinyl, and the like.

(v) The substituents of the optionally substituted aromatic heterocyclic group, the optionally substituted pyridyl, the optionally substituted tetrazolyl, the optionally substituted pyrazinyl, the optionally substituted pyrimidinyl, and the optionally substituted thiazolyl may be the same or different and may be one up to the maximum possible number of, preferably e.g. 1 or 2, substituents selected from the group consisting of halogen, hydroxy, sulfanyl, nitro, cyano, carboxy, carbamoyl, $C_{1-10}$ alkyl, trifluoromethyl, $C_{3-8}$ cycloalkyl, $C_{6-10}$ aryl, an aliphatic heterocyclic group, an aromatic heterocyclic group, $C_{1-10}$ alkoxy, $C_{3-8}$ cycloalkoxy, $C_{6-14}$ aryloxy, $C_{7-16}$ aralkyloxy, $C_{2-11}$ alkanoyloxy, $C_{7-15}$ aroyloxy, $C_{1-10}$ alkylsulfanyl, $-NR^{X1}R^{Y1}$ (wherein $R^{X1}$ and $R^{Y1}$ may be the same or different and each represents a hydrogen atom, $C_{1-10}$ alkyl, $C_{3-8}$ cycloalkyl, $C_{6-14}$ aryl, an aromatic heterocyclic group, $C_{7-16}$ aralkyl, $C_{2-11}$ alkanoyl, $C_{7-15}$ aroyl, $C_{1-10}$ alkoxy carbonyl, or $C_{7-16}$ aralkyloxy carbonyl), $C_{2-11}$ alkanoyl, $C_{7-15}$ aroyl, $C_{1-10}$ alkoxy carbonyl, $C_{6-14}$ aryloxy carbonyl, $C_{1-10}$ alkyl carbamoyl, and di-$C_{1-10}$ alkylcarbamoyl.

In the groups exemplified in the above (v);
Examples of the $C_{1-10}$ alkyl and the $C_{1-10}$ lower alkyl moieties of the $C_{1-10}$ alkoxy, the $C_{2-11}$ alkanoyloxy, the $C_{1-10}$ alkyl sulfanyl, the $C_{2-11}$ alkanoyl, the $C_{1-10}$ alkoxy carbonyl, the $C_{1-10}$ alkyl carbamoyl and the di-$C_{1-10}$ alkylcarbamoyl include the groups listed for the above lower alkyl (i). The two lower alkyl moieties of the di-$C_{1-10}$ alkylcarbamoyl may be the same or different from each other.

Examples of the $C_{3-8}$ cycloalkyl and the cycloalkyl moiety of the $C_{3-8}$ cycloalkoxy include the groups listed for the above cycloalkyl (iii).

Examples of the $C_{6-14}$ aryl and the aryl moieties (vi) of the $C_{6-14}$ aryloxy, $C_{7-15}$ aroyl, $C_{7-15}$ aroyloxy and the $C_{6-14}$ aryloxy carbonyl include aryl having 6 to 14 carbon atoms, more specifically, phenyl, naphthyl, azulenyl, anthryl, and the like.

Examples of the aryl moieties of the $C_{7-16}$ aralkyl, the $C_{7-16}$ aralkyloxy, and the $C_{7-16}$ aralkyloxy carbonyl include the group listed for the above aryl moieties (vi), and the examples of the alkyl moieties include $C_{1-10}$ alkylene, more specifically, a group formed by removing a hydrogen atom from the groups listed for the above lower alkyl (i).

The halogen means a fluorine atom, a chlorine atom, a bromine atom, or an iodine atom.

Examples of the aliphatic heterocyclic group include a 5- or 6-membered monocyclic aliphatic heterocyclic group containing at least one heteroatom selected from a nitrogen atom, an oxygen atom and a sulfur atom; a bicyclic or tricyclic aliphatic heterocyclic group in which 3- to 8-membered rings are fused and which contains at least one heteroatom selected from a nitrogen atom, an oxygen atom and a sulfur atom; and the like, more specifically, aziridinyl, azetidinyl, pyrrolidinyl, piperidino, piperidinyl, azepanyl, 1,2,5,6-tetrahydropyridyl, imidazolidinyl, pyrazolidinyl, piperazinyl, homopiperazinyl, pyrazolinyl, oxiranyl, tetrahydrofuranyl, tetrahydro-2H-pyranyl, 5,6-dihydro-2H-pyranyl, oxazolidinyl, morpholino, morpholinyl, thioxazolidinyl, thiomorpholinyl, 2H-oxazolyl, 2H-thioxazolyl, dihydroindolyl, dihydroisoindolyl, dihydrobenzofuranyl, benzimidazolidinyl, dihydrobenzoxazolyl, dihydrobenzothioxazolyl, benzodioxolinyl, tetrahydroquinolyl, tetrahydroisoquinolyl, dihydro-2H-chromanyl, dihydro-1H-chromanyl, dihydro-2H-thiochromanyl, dihydro-1H-thiochromanyl, tetrahydroquinoxalinyl, tetrahydroquinazolinyl, dihydrobenzodioxanyl, and the like.

Examples of the aromatic heterocyclic group include the groups listed for the above aromatic heterocyclic group (iv).

Examples of a pharmaceutically acceptable salt of compound (I) include pharmaceutically acceptable acid addition salts, metal salts, ammonium salts, organic amine addition salts, amino acid addition salts, and the like. Examples of the acid addition salts include inorganic acid salts such as hydrochlorides, sulfates, and phosphates; organic acid salts such as acetates, trifluoroacetates, maleates, fumarates, tartrates, citrates, and lactates; and the like. Examples of the metal salts include alkali metal salts such as sodium salts and potassium salts; alkaline earth metal salts such as magnesium salts and calcium salts; aluminum salts; zinc salts; and the like. Examples of the ammonium salts include salts of ammonium, tetramethylammonium, and the like. Examples of the organic amine addition salts include addition salts of morpholine, piperidine, and the like. Examples of the amino acid addition salts include addition salts of lysine, glycine, phenylalanine, aspartic acid, glutamic acid, and the like.

When one or more of compounds (I) of the present invention or pharmaceutically acceptable salts thereof are (1) added to cells and the like, in an in vitro system or (2) administered to a living body such as mammals, the production of kynurenine in the in vitro system or the living body is inhibited as compared with the case where the compound or pharmaceutically acceptable salt thereof is not administered. That is, compound (I) or a pharmaceutically acceptable salt thereof has an inhibitory effect on the production of kynurenine and consequently has an inhibitory effect on the increase in the kynurenine level. Compound (I) or a pharmaceutically acceptable salt, thereof has excellent inhibitory effect on the production of kynurenine and therefore is useful for, for example, prevention or treatment of a disease in which IDO and/or kynurenine is involved. Compound (I) or a pharmaceutically acceptable salt thereof is especially suitable as an active ingredient of a preventive or therapeutic agent for a disease associated with the production of kynurenine, for example, a disease in which the local or systemic level of kynurenine is increased, and is also suitable as an active ingredient of a kynurenine production inhibitor. In particular, compound (1) or a pharmaceutically acceptable salt thereof is suitable as an active ingredient of a preventive or therapeutic agent for diseases such as cancers (tumors), immune diseases, neurodegenerative diseases, and infections.

The term "treatment" refers to alleviating or curing a condition or a disease and/or its accompanying symptom, and to alleviating the same. The term "prevention" refers to delaying or preventing the development of a condition or a disease and its accompanying symptom, or to reducing the subject's risk of developing a condition or a disease.

Examples of the disease associated with IDO and/or kynurenine production include cancers (tumors), immune diseases, neurodegenerative diseases, infections, and the like.

Examples of the cancers (tumors) include hematopoietic tumor, multiple myeloma, breast cancer, ovarian cancer, endometrial cancer, cervical cancer, prostate cancer, bladder cancer, renal cancer, gastric cancer, esophagus cancer, hepatic cancer, biliary tract cancer, colon cancer, rectal cancer, pancreatic cancer, lung cancer, head and neck cancer, osteosarcoma, melanoma, brain tumor, and the like. Among these, compound (I) or a pharmaceutically acceptable salt thereof is suitable for the prevention or treatment of gastric cancer, breast cancer, and the like.

Examples of the immune diseases include acquired immune deficiency syndrome (AIDS), bronchial asthma, pollen allergy, allergic rhinitis, atopic dermatitis, rheumatoid arthritis, ulcerative colitis, Crohn's disease, multiple sclerosis, amyotrophic lateral sclerosis, graft versus host disease, and the like.

Examples of the neurodegenerative diseases include AIDS dementia, Alzheimer's disease, depression, and the like.

Examples of the infections include viral infection, bacterial infection, fungal infection, chlamydial infection, rickettsial infection, and the like.

The above compound (I) or a pharmaceutically acceptable salt thereof is especially suitable as an active ingredient for a preventive or therapeutic agent for cancers (tumors), and the like.

Next, production methods of compound (1) are explained in the following.

In the production methods described below, in cases where a defined group changes under the conditions in which the methods are performed or is not suitable for carrying out the methods, introduction and removal of a protective group, which is commonly used in synthetic organic chemistry, and the like may be performed (for example, in accordance with the method described in T. W. Greene, Protective Groups in Organic Synthesis, 3rd edition, John Wiley & Sons Inc. (1999)) to produce a desired compound. If necessary, the order of the reaction steps, such as introduction of a substituent, can also be changed.

Compound (I) can be produced according to, for example, the following Production Methods 1 to 5.

Production Method 1

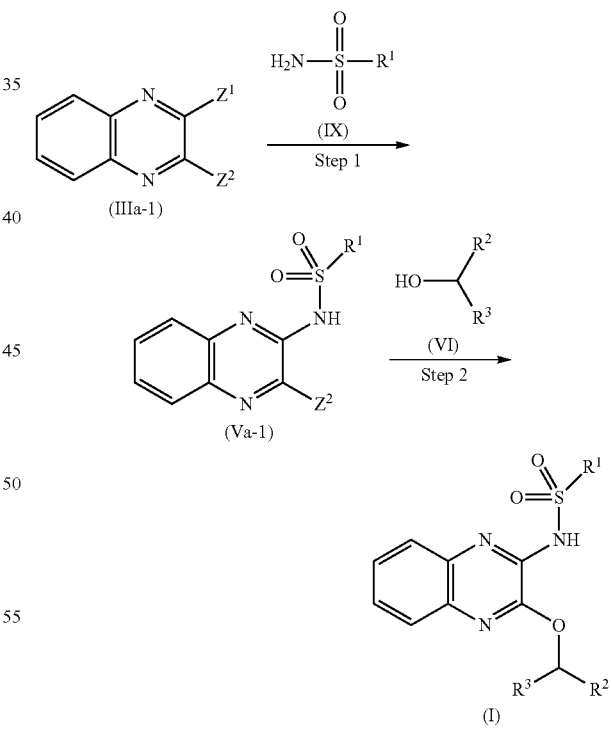

(wherein, $R^1$, $R^2$ and $R^3$ have the same meanings as defined above, respectively, and $Z^1$ and $Z^2$ may be the same or different and each represents a leaving group, such as a chlorine atom, a bromine atom, an iodine atom, methanesulfonyloxy, p-toluenesulfonyloxy, and trifluoromethanesulfonyloxy.)

Step 1

Compound (Va-1) can be produced by reacting compound (IIIa-1) with 1 to 10 equivalents, preferably 1 equivalent, of compound (IX) in the absence of a solvent or in a solvent inert to the reaction in the presence of 1 to 100 equivalents, preferably 1 to 5 equivalents, of a suitable base at a temperature between −10° C. and 200° C., preferably between 30° C. and 180° C., for 5 minutes to 72 hours.

Examples of the solvent inert to the reaction include tetrahydrofuran (THF), dioxane, 1,2-dimethoxyethane, benzene, toluene, xylene, N,N-dimethylformamide (DMF), N,N-dimethylacetamide (DMA), dimethyl sulfoxide (DMSO), N-methylpyrrolidone (NMP), pyridine, chloroform, dichloromethane, ethyl acetate, acetonitrile, and the like, and these can be used alone or as a mixture thereof. Among these, preferred is DMSO or DMF.

Examples of the suitable base include alkali metal hydrides, such as sodium hydride and potassium hydride; metal alkoxides, such as sodium methoxide, sodium ethoxide and potassium tert-butoxide; organometallic bases, such as n-butyllithium, sec-butyllithium and tert-butyllithium; metal amides, such as lithium diisopropylamide (LDA) and lithium hexamethyldisilazane (LiHMDS); alkali metal salts, such as sodium hydroxide, potassium hydroxide, lithium hydroxide, sodium carbonate and potassium carbonate; organic bases, such as pyridine, triethylamine, diisopropylethylamine, 1,8-diazabicyclo[5.4.0]undec-7-ene (DBU), 1,5-diazabicyclo[4.3.0]non-5-ene (DBN), N,N-dimethylaminopyridine (DMAP) and N-methylmorpholine; solid bases, such as AMBERLYST A-21 (Rohm and Haas Company), AG1-X8 (Bio-Rad Laboratories, Inc.), polyvinylpyridine and morpholinomethyl polystyrene; and the like. Among these, preferred are alkali metal hydrides, alkali metal salts, or the like. More preferred are sodium hydride, potassium carbonate, or the like.

Compound (IIIa-1) can be obtained as, for example, a commercial product, or according to known methods (for example, the method described in WO 2003/059893, Journal of Medicinal Chemistry, vol. 24, pp. 93-101 (1981), and the like).

Compound (IX) can be obtained as, for example, a commercial product.

Step 2

Compound (I) can be produced by reacting compound (Va-1) with 1 to 20 equivalents, preferably 1 to 4 equivalents, of compound (VI) in the absence of a solvent or in a solvent inert to the reaction in the presence of 1 to 100 equivalents, preferably 1 to 10 equivalents, of a suitable base at a temperature between −20° C. and 200° C., preferably between room temperature and 80° C., for 5 minutes to 72 hours.

Examples of the solvent inert to the reaction include THF, dioxane, 1,2-dimethoxyethane, benzene, toluene, xylene, DMF, DMA, NMP, pyridine, chloroform, dichloromethane, ethyl acetate, acetonitrile, and the like, and these can be used alone or as a mixture thereof. Among these, preferred is THF or DMF.

Examples of the suitable base include alkali metal hydrides, such as sodium hydride and potassium hydride; metal alkoxides, such as sodium methoxide, sodium ethoxide and potassium tert-butoxide; organometallic bases, such as n-butyllithium, sec-butyllithium and tert-butyllithium; metal amides, such as LDA and LiHMDS; alkali metal salts, such as sodium hydroxide, potassium hydroxide, lithium hydroxide, sodium carbonate and potassium carbonate; organic bases, such as pyridine, triethylamine, diisopropylethylamine, DBU, DBN, DMAP and N-methylmorpholine; solid bases, such as AMBERLYST A-21 (Rohm and Haas Company), AG1-X8 (Bio-Rad Laboratories, Inc.), polyvinylpyridine and morpholinomethyl polystyrene; and the like. Among these, preferred are alkali metal hydrides, metal alkoxides, or the like. More preferred are sodium hydride, potassium tert-butoxide, or the like.

Compound (VI) can be obtained according to known methods (for example, Journal of the American Chemical Society, vol. 111, p. 393 (1939), and the like), or as a commercial product.

Production Method 2

[Chemical Formula 15]

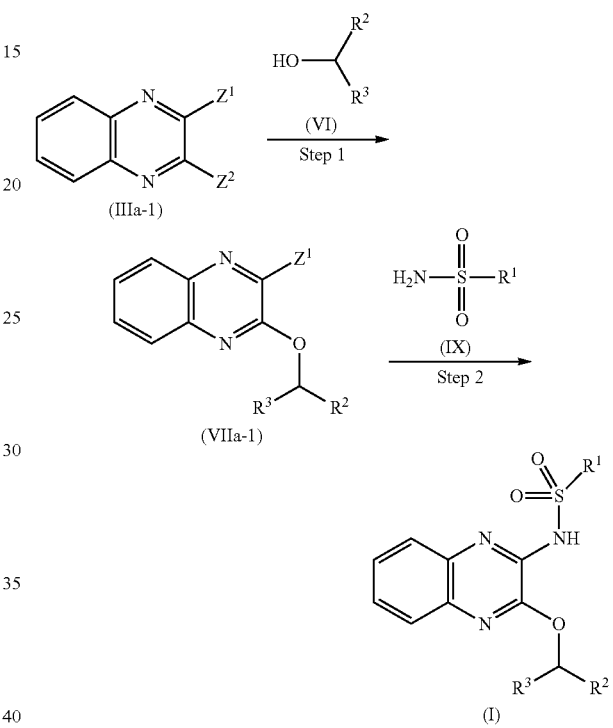

(wherein, $R^1$, $R^2$, $R^3$, $Z^1$ and $Z^2$ have the same meanings as defined above, respectively.)

Step 1

Compound (VIIa-1) can foe produced in the same manner as in Step 2 of Production Method 1, using compound (IIIa-1).

Step 2

Compound (I) can be produced in the same manner as in Step 1 of Production Method 1, using compound (IIIa-1).

Production Method 3

[Chemical Formula 16]

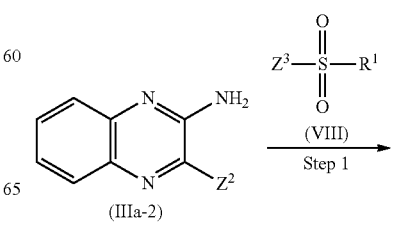

-continued

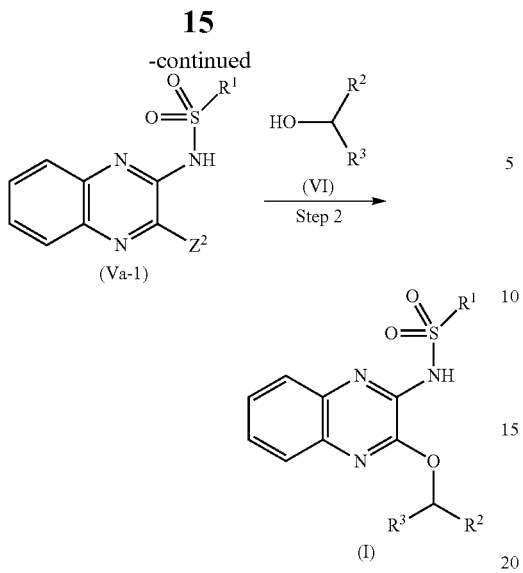

(wherein, $R^1$, $R^2$, $R^3$ and $Z^2$ have the same meanings as defined above, respectively, and $Z^3$ represents a leaving group, such as a chlorine atom, a bromine atom, an iodine atom, methanesulfonyloxy, p-toluenesulfonyloxy, or trifluoromethanesulfonyloxy.)

Step 1

Compound (Va-1) can be produced by reacting compound (IIIa-2) with 1 to 10 equivalents, preferably 1 equivalent, of compound (VIII) in the absence of a solvent or in a solvent inert to the reaction in the presence of 1 to 100 equivalents, preferably 1 to 5 equivalents, of a suitable base at a temperature between −10° C. and 200° C., preferably between 30° C. and 180° C., for 5 minutes to 72 hours.

Examples of the solvent inert to the reaction include THF, dioxane, 1,2-dimethoxyethane, benzene, toluene, xylene, DMF, DMA, DMSO, NMP, pyridine, chloroform, dichloromethane, ethyl acetate, acetonitrile, and the like, and these can be used alone or as a mixture thereof. Among these, preferred are DMSO, DMF, and the like.

Examples of the suitable base include alkali metal hydrides, such as sodium hydride and potassium hydride; metal alkoxides, such as sodium methoxide, sodium ethoxide and potassium tert-butoxide; organometallic bases, such as n-butyllithium, sec-butyllithium and tert-butyllithium; metal amides, such as LDA and LiHMDS; alkali metal salts, such as sodium hydroxide, potassium hydroxide, lithium hydroxide, sodium carbonate and potassium carbonate; organic bases, such as pyridine, triethylamine, diisopropylethylamine, DBU, DBN, DMAP and M-methylmorpholine; solid bases, such as AMBERLYST A-21 (Rohm and Haas Company), AG1-X8 (Bio-Pad Laboratories, Inc.), polyvinylpyridine and morpholinomethyl polystyrene; and the like. Among these, preferred are alkali metal hydrides. More preferred are sodium hydride or the like.

Compound (IIIa-2) can be obtained, for example, as a commercial product, or according to known methods (for example, the method described in U.S. Pat. No. 3,898,216, WO 2010124326, and the like).

Compound (VIII) can be obtained, for example, as a commercial product.

Step 2

Compound (I) cars be produced in the same manner as in Step 2 of Production Method 1, using compound (Va-1).

Production Method 4

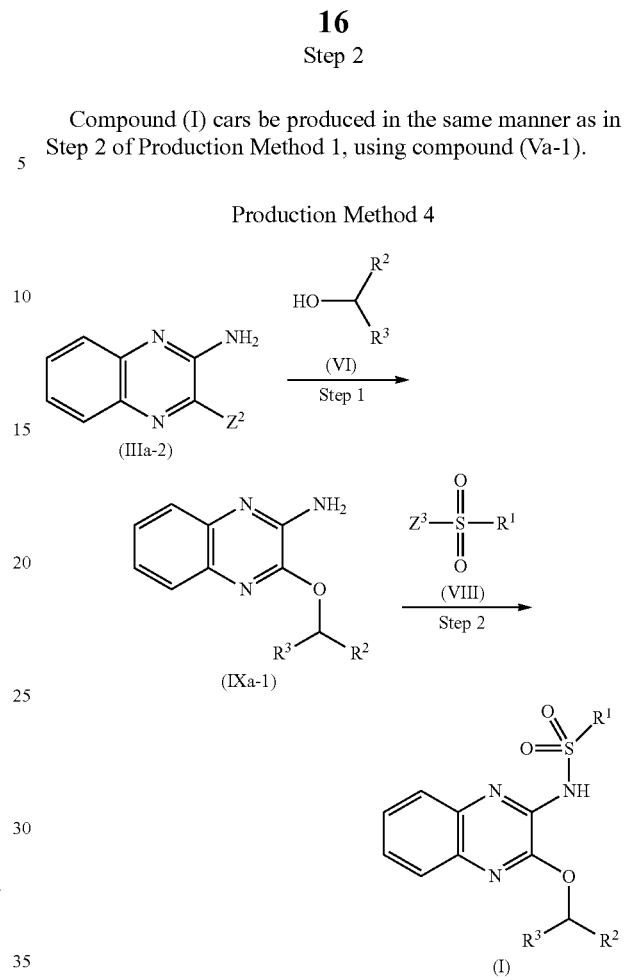

(wherein, $R^1$, $R^2$, $R^3$, $Z^2$ and $Z^3$ have the same meanings as defined above, respectively.)

Step 1

Compound (IXa-1) can be produced in the same manner as in Step 2 of Production Method 1, using compound (IIIa-2).

Step 2

Compound (I) can be produced in the same manner as in Step 1 of Production Method 3, using compound (IXa-1).

Production Method 5

[Chemical Formula 18]

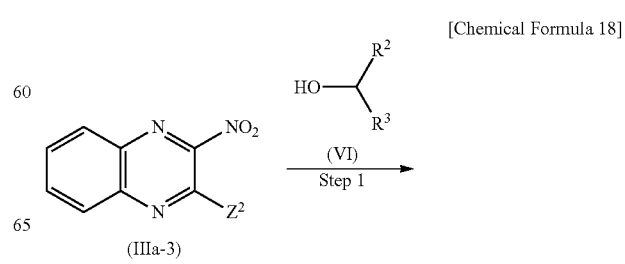

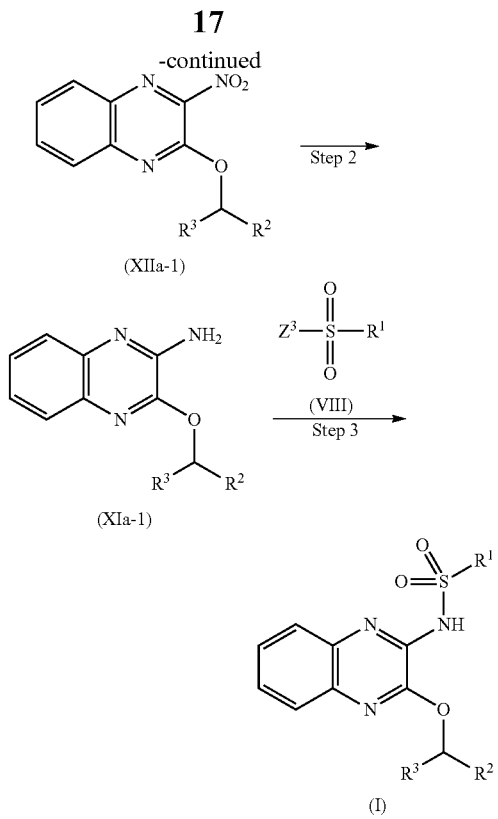

(wherein, $R^1$, $R^2$, $R^3$, $Z^2$ and $Z^3$ have the same meanings as defined above, respectively.)

Step 1

Compound (XIIa-1) can be produced in the same manner as in Step 2 of Production Method 1, using compound (IIIa-3).

Step 2

Compound (XIa-1) can be produced by treating compound (XIIa-1) with 10 to 100% by weight of a reducing agent in the absence of a solvent or in a solvent inert to the reaction at a temperature between −20° C. and 200° C., preferably between room temperature and 80° C., for 5 minutes to 72 hours.

Examples of the solvent inert to the reaction include water, acetic acid, hydrochloric acid, trifluoroacetic acid, trifluoromethanesulfonic acid, methanol, ethanol, propanol, THF, dioxane, ether, 1,2-dimethoxyethane, benzene, toluene, xylene, DMF, DMA, NMP, pyridine, and the like, and these solvents can be used alone or as a mixture thereof. Among these, preferred are water, acetic acid, and a combination thereof.

Examples of the reducing agent include iron(0), tin(0), tin(II) dichloride, tin(II) dichloride dihydrate, zinc, sodium hydrosulfite, or the like. Among these, preferred are iron(0) or the like.

Step 3

Compound (I) can foe produced in the same manner as in Step 1 of Production Method 3, using compound (XIa-1).

Among compounds (I), an enantiomer of compound (I) having a chiral center on the C (carbon atom) of —CH($R^2$) ($R^3$) can be obtained by subjecting the compounds (I) obtained by Production Methods 1 to 5 to chromatography using an optically active column or subjecting them to optical resolution using enzymatic reaction. Alternatively, the enantiomer can be obtained by converting a racemic compound (I) into the corresponding diastereomers or diastereomeric salts via reaction with an optical resolving agent, isolating a desired diastereomer by crystallization, various kinds of chromatography, or the like, and finally performing deprotection, desalination or the like. Further alternatively, the enantiomer of compounds (I) can be obtained by subjecting compound. (VIIa-1) obtained by Production Method 2, compound (IXa-1) obtained by Production Method 4, or compound (XIIa-1) or compound (XIa-1) obtained by Production Method 5 to chromatography using an optically active column or subjecting it to optical resolution using enzymatic reaction to produce the corresponding enantiomer, and then subjecting the resulting enantiomer to the next step of each Production Method.

Further alternatively, the enantiomer can be obtained by using an enantiomer of compound (VI) in Production Methods 1 to 5. The enantiomer of compound (VI) can be obtained as a commercial product or according to known methods (for example, WO 98/42643 and the like).

Isolation and purification of the intermediates and the desired compounds in each Production Method can foe performed by an appropriate combination of methods generally employed in organic synthesis, for example, filtration, extraction, washing, drying, concentration, crystallization, various types of chromatography, and the like. The intermediates can be subjected to the subsequent reaction without any particular purification.

Some of compounds (I) exist as isomers such as tautomers, stereoisomers, regioisomers, geometric isomers, and enantiomers. All possible isomers and mixtures containing the isomers at any ratio are also included in the present invention.

When desired, a salt of compound (I) can be obtained, as follows. When compound (I) is obtained in the form of a salt, the salt may be directly purified. When compound (I) is obtained in the free form, the compound may be dissolved or suspended in a suitable solvent, made into a salt by addition of an acid or a base, or the like, and isolated and purified.

Compound (I) and a pharmaceutically acceptable salt thereof may exist in the form of adducts with water or any of various solvents in some cases, and these adducts are also included in the present invention.

Specific examples of the compounds of the present invention are shown in Tables 1 to 4. However, the scope of the present invention is not limited to these compounds.

In the following Tables, Me represents methyl.

TABLE 1

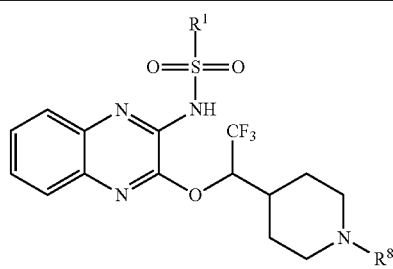

| Example | Compound | $R^1$ | $R^8$ |
|---|---|---|---|
| 1 | 1 | (*-CH₂CH₂-Me) | (pyridine-N,N-dimethylcarboxamide*) |

TABLE 1-continued

| Example | Compound | R¹ | R⁸ |
|---|---|---|---|
| 2 | 2 | *-propyl (Me) | 2-(N,N-dimethylcarbamoyl)pyridin-3-yl |
| 3 | 3 | *-propyl (Me) | 6-(N,N-dimethylcarbamoyl)pyridin-2-yl |
| 4 | 4 | *-propyl (Me) | 6-cyanopyridin-3-yl |
| 5 | 5 | *-propyl (Me) | 6-carbamoylpyridin-3-yl |
| 6 | 6 | *-propyl (Me) | 4-cyanopyridin-2-yl |
| 7 | 7 | *-propyl (Me) | 5-cyanopyridin-3-yl |
| 8 | 8 | *-propyl (Me) | 6-(N,N-dimethylcarbamoyl)pyridin-3-yl |
| 9 | 9 | *-propyl (Me) | 3-cyanopyridin-2-yl |
| 10 | 10 | *-propyl (Me) | 3-carbamoylpyridin-2-yl |
| 11 | 11 | *-propyl (Me) | 2-methyl-2H-tetrazol-5-yl |

TABLE 2

| Example | Compound | R¹ | R⁸ |
|---|---|---|---|
| 12 | 12 | *-propyl (Me) | 1-methyl-1H-tetrazol-5-yl |
| 13 | 13 | *-propyl (Me) | pyrazin-2-yl |
| 14 | 14 | *-propyl (Me) | pyrimidin-5-yl |

TABLE 2-continued

[Structure: quinoxaline with R¹-SO2-NH- group and -O-CH(CF3)-piperidine-N-R⁸ substituent]

| Example | Compound | R¹ | R⁸ |
|---|---|---|---|
| 15 | 15 | *−CH2CH2−Me (propyl) | 5-cyano-pyridin-2-yl |
| 16 | 16 | propyl | 2-cyano-pyridin-4-yl |
| 17 | 17 | propyl | 3-cyano-pyridin-4-yl |
| 18 | 18 | propyl | thiazol-2-yl |
| 19 | 19 | propyl | 6-methyl-pyridine-3-carboxamide (5-carbamoyl-6-methyl-pyridin-2-yl) |
| 20 | 20 | propyl | pyridin-2-yl |
| 21 | 21 | propyl | pyridin-3-yl |
| 22 | 22 | propyl | pyridin-4-yl |

TABLE 3

[Structure: quinoxaline with R¹-SO2-NH- group and -O-CH(CF3)-R⁹ substituent]

| Example | Compound | R¹ | R⁹ |
|---|---|---|---|
| 23 | 23 | −CH2CH2−OMe | 2-(5-cyclopropyl-1,2,4-oxadiazol-3-yl)pyridin-5-yl |
| 24 | 24 | −CH2CH2−OMe | 2-(5-methoxymethyl-1,2,4-oxadiazol-3-yl)pyridin-5-yl |
| 25 | 25 | propyl (−CH2CH2−Me) | 2-(5-cyclopropyl-1,2,4-oxadiazol-3-yl)pyridin-5-yl |
| 26 | 26 | propyl | 2-(5-methoxymethyl-1,2,4-oxadiazol-3-yl)pyridin-5-yl |
| 27 | 27 | −CH2CH2−OMe | 2-(5-methyl-1,2,4-oxadiazol-3-yl)pyridin-5-yl |

TABLE 4
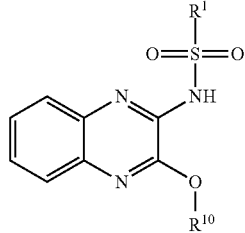
| Example | Compound | R¹ | R¹⁰ | R⁹ |
|---|---|---|---|---|
| 28 | 28 | 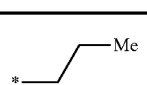 | 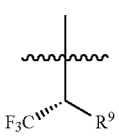 | 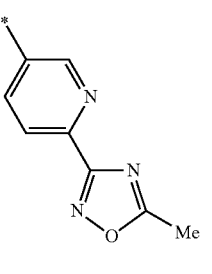 [SMILES: *c1ccc(-c2noc(C)n2)nc1] |
|  | 29 |  | 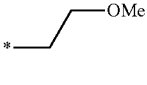 | 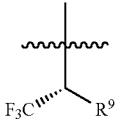 |
| 29 | 30 | 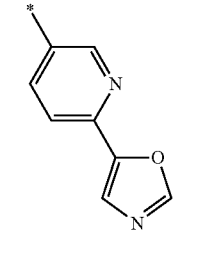 [SMILES: *c1ccc(-c2cnco2)nc1] | 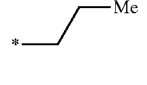 | 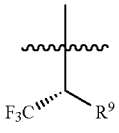 |
|  | 31 |  |  | 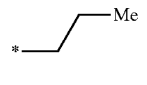 |
| 30 | 32 | 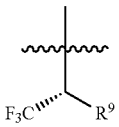 | 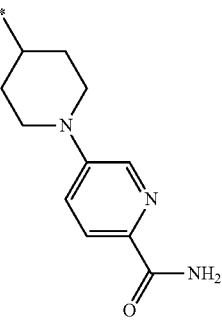 |  |
|  | 33 |  |  |  |
| 31 | 34 |  |  |  |
|  | 35 |  |  |  |

TABLE 4-continued

[Quinoxaline sulfonamide core structure with R¹ on sulfonyl, R¹⁰ on oxygen, R⁹ substituent]

| Example | Compound | R¹ | R¹⁰ | R⁹ |
|---|---|---|---|---|
| 32 | 36 | *—OMe | *—C(F₃C)(R⁹)H | 5-pyridyl |
| | 37 | | *—C(F₃C)(R⁹)H (stereo) | 3-cyclopropyl-1,2,4-oxadiazol-5-yl |

Next, pharmacological effects of compound (I) are explained by Test Example 1.

Test Example 1

Inhibitory Activity on the Production of Kynurenine

This assay was performed by a modification of the method described in J. Biol. Chem., vol. 263, pp. 2041-2048 (1938). For culture of the human gastric cancer cell line KATO-XXX, RPMI 1640 (GIBCO, 11875) supplemented with 10 vol % FBS (GIBCO, 10091-148, lot. 665285) was used. One μL of a test substance in a DMSO solution was diluted with 199 μL of the culture medium and placed in wells of a 384-well plate (10 μL/well). Next, IFN-γ (Sigma, I-3265) was added to a fresh culture medium to a concentration of 31.25 ng/mL, and KATO-III cells were suspended at 50,000 cells/mL in the culture medium. Forty μL of the suspension was added to each well (2,000 cells/well) and cultured under 5% $CO_2$ at 37° C. for 96 hours. The final concentration of DMSO was limited to 0.1 vol % or less so that DMSO itself may not affect the kynurenine concentration measured in this assay. After the culture, 10 μL of a 30 w/v % aqueous trichloroacetic acid solution was added to each well, and incubation was performed at 65° C. for 30 minutes. The plate was centrifuged at 2,500×g for 5 minutes and 15 μL of the supernatant in each well was transferred into another 384-well plate. To the transferred supernatant, 15 μL of a 2 w/v % solution of p-dimethylaminobenzaldehyde in acetic acid was added, incubation was performed at 65° C. for 20 minutes and the absorbance was measured at 480 nm.

[Formula 1]

$$\text{Inhibition \%} = \frac{(\text{Control} - \text{Sample})}{(\text{Control} - \text{Blank})} \times 100 \quad \text{(formula A1)}$$

Sample: the absorbance value of the well to which DMSO solution containing a test substance was added and in which the cells were treated with IFN-γ.

Blank: the absorbance value of the well to which DMSO not containing a test substance was added and in which the cells were treated with IFN-γ.

Control: the absorbance value of the well to which DMSO not containing a test substance was added and in which the cells were not treated with IFN-γ.

The inhibition % of each test compound was calculated by formula A1. As a result, for example, compounds 1 to 21, 23 to 28, 30, 32, 34, 36 and 37 at a concentration of 10 μmol/L showed the inhibition % of 80% or more.

That is, the results revealed that compounds (I) of the present invention have an inhibitory activity on the production of kynurenine.

In this assay, the expression of IDO in KATO-III cells is induced by IFN-γ treatment, and kynurenine in the culture medium is quantified. The kynurenine concentration in a culture medium is known to increase in proportion to the enzymatic activity of intracellular IDO (for example, J. Biol. Chem., vol. 263, pp. 2041-2048 (1988)). The compounds of the present invention showed an inhibitory effect on the production of kynurenine. The production of kynurenine is known to be inhibited by IDO inhibitors (for example, J. Clin. Invest., vol. 117, No. 5, pp. 1147-1154 (1988)), and thus it is speculated that compounds (I) also have an inhibitory effect on IDO.

Compounds having an inhibitory effect on the production of kynurenine and/or on IDO are known to foe useful as an antitumor agent, an anti-AIDS agent, an anti-AIDS dementia agent, an anti-Alzheimer's disease agent, an antidepressant, or the like (for example, J. Clin. Invest., vol. 117, pp. 1147-1154 (2007); J. Virol., vol. 81, pp. 11593-11603 (2007); Neuropathol. Appl. Neurobiol., vol. 31, pp. 395-404 (2005); Neurosci. Lett., vol. 187, pp. 9-12 (1995); and Neuropsychopharmacology, vol. 33, 2341-2351 (2008)). Such compounds are known to also have an immunostimulatory activity (for example, Nat. Immunol., vol. 2, pp. 64-68 (2001)). Therefore compounds (I) of the present invention are useful as an antitumor agent, an anti-AIDS agent, an anti-AIDS dementia agent, an anti-Alzheimer's disease agent, an antidepressant, an immunostimulator, or the like.

Next, the ability of compounds (I) to induce cytochrome P-450 3A4 (CYP3A4) are explained by Test Example 2.

Test Example 2

Experimental Method for Induction of CYP3A4 using HepaRG (Registered Trademark) Cells CYP3A4-inducing activity was evaluated using HepaRG cells (Biopredic international). HepaRG cells were suspended in a medium at a concentration of $0.72 \times 10^6$ cells/mL and added in a volume of 100 µL to each well of a 96-well collagen coated plate (Biopredic international). The medium used for seeding HepaRG cells was HepaRG Thawing and Seeding Medium 670 (Biopredic international) and the medium used during treatment with a test compound was HepaRG Serum-free Induction Medium 650 (Biopredic international). Three days after the seeding of HepaRG cells, treatment with a test compound was started. After 200 µL of HepaRG Serum-free Induction Medium 650 was added to each well of the 96-well, collagen plate, a test compound dissolved in dimethylsulfoxide (DMSO) was added in a volume of 0.5 µL to each well so that the final concentration was 1 µmol/L. The well to which only DMSO was added was used as a negative control. The medium in the wells containing the test compound was replaced every 24 hours and the treatment with the test compound was continued for 72 hours. The fourth day after the start of the treatment with the test compound, midazolam, which is a typical substrate for CYP3A4, was added and CYP3A4-inducing activity was evaluated by measuring changes in the metabolic activity. The medium was removed by suction and each well was washed twice with PBS (150 µL/well) warmed to 37° C. HepaRG Serum-free Induction Medium 650 containing 20 µmol/L midazolam was warmed to 37° C. and added in a volume of 100 µL to each well. The plate was incubated in a $CO_2$ incubator for 2 hours. At the end of the reaction, 70 µL of the reaction medium was recovered from each well and mixed with 70 µL of a methanol solution containing an internal standard (propranolol, 2 µmol/L). The mixture was centrifuged (at 5000×g at 4° C. for 10 minutes) and the supernatant was used as an analysis sample. The midazolam metabolizing activity was evaluated by measuring the amount of a produced metabolite by CYP3A4, 1'-hydroxymidazolam, by means of a liquid chromatograph-tandem mass spectrometry (LC-MS/MS). Agilent 1100 series (Agilent technologies) was used as the LC device, API2000 (AB sciex) was used as the MSMS device, and HTC PAL (CTC analytics) was used as the autosampler. CAPCELL PAK C18 ACR column (3 µm, 3 mm (I. D.)×35 mm, purchased from Shiseido Co., Ltd.) was used as the analytical column. The mobile phase A was 10 mmol/L aqueous ammonium acetate solution and the mobile phase B was methanol. The gradient conditions were 0 min (B=30%), 0.2 min (B=30%), 2.2 min (B=95%), 4 min (B=95%), 4.01 min (B=30%), 5 min (B=30%). The flow rate was 0.6 mL/min and the sample injection volume was 30 µL. The ions were detected by atmospheric pressure ionization mode using the MSMS device. The detection was performed by multiple reaction monitoring and the 1'-hydroxy midazolam ions were detected at m/z (precursor ion>product ion)=342.1>168.2.

Calculation of Fold Induction

The fold induction by each test compound was determined by using formula A2 below, which is for calculating the fold induction as the ratio of the metabolic activity in the test compound-treatment group to that of the negative control group (DMSO-treatment group). The results are shown in Table 5.

[Formula 2]

$$\text{Fold Induction (fold)} = \frac{\text{Amount of produced 1'-hydroxy midazolam in test compound } X\text{-treatment group}}{\text{Amount of produced 1'-hydroxy midazolam in control group}} \quad \text{(formula A2)}$$

TABLE 5

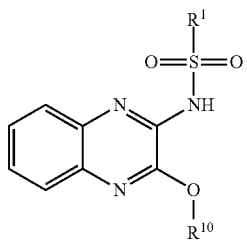

| International publication No. or International application No. | Compound No. in Examples | $R^1$ | $R^{10}$ | Fold induction |
|---|---|---|---|---|
| WO2010/053182 | 192 | 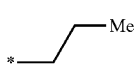 | 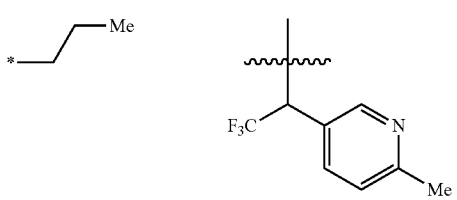 | 7.80 |

TABLE 5-continued
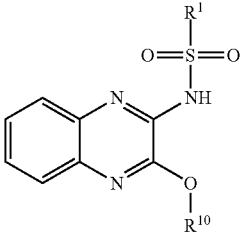
| International publication No. or International application No. | Compound No. in Examples | R¹ | R¹⁰ | Fold induction |
|---|---|---|---|---|
| | 319 | 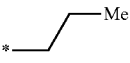 | 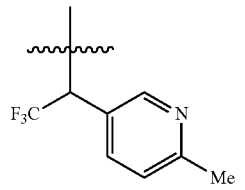 [SMILES: *C(c1ccc(C)nc1)C(F)(F)F] | 6.59 |
| PCT/JP2011/060654 (WO2011/142316) | 66 | 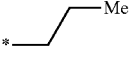 | 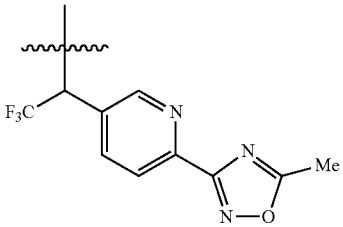 [SMILES: *C(c1ccc(-c2noc(C)n2)nc1)C(F)(F)F] | 1.80 |
| | 73 | 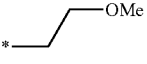 | 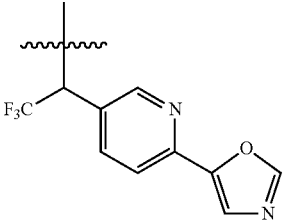 [SMILES: *C(c1ccc(-c2cnco2)nc1)C(F)(F)F] | 1.35 |
| Present application | 25 | 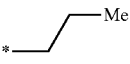 | 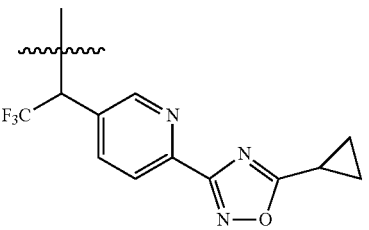 [SMILES: *C(c1ccc(-c2noc(C3CC3)n2)nc1)C(F)(F)F] | 1.41 |
| | 27 | 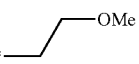 | 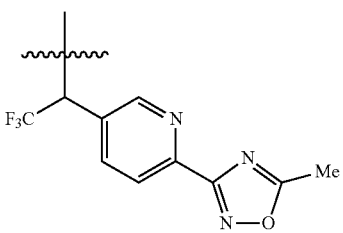 [SMILES: *C(c1ccc(-c2noc(C)n2)nc1)C(F)(F)F] | 1.21 |

TABLE 5-continued

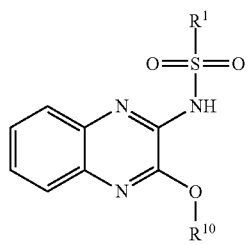

| International publication No. or International application No. | Compound No. in Examples | R¹ | R¹⁰ | Fold induction |
|---|---|---|---|---|
| | 28 | *–CH₂CH₂–Me | –C(CF₃)(H)–[5-(5-methyl-1,2,4-oxadiazol-3-yl)pyridin-2-yl] | 1.27 |
| | 30 | *–CH₂CH₂–OMe | –C(CF₃)(H)–[5-(oxazol-5-yl)pyridin-2-yl] | 1.12 |
| | 37 | *–CH₂CH₂–OMe | –C(CF₃)(H)–[5-(5-cyclopropyl-1,2,4-oxadiazol-3-yl)pyridin-2-yl] | 1.33 |

The above results revealed that compounds 25, 27, 28 and 37 of the present application showed lower fold inductions than the structural analog, compound 66, described in PCT/JP2011/060654 (WO 2011/142316) and that compounds 25, 27, 28 and 37 thus had lower CYP3A4-inducing activity. Also revealed is that compound 30 of the present application showed a lower fold induction than the corresponding racemic compound 73 described in PCT/JP2011/060654 (WO 2011/142316) and that compound 30 thus had lower CYP3A4-inducing activity.

One of the causes of drug interactions is the induction of metabolic enzymes. Among the enzymes, CYP3A4 metabolizes a wide range of medicinal drugs. In cases where the induction of CYP3A4 by a drug leads to enhanced metabolism of the drug itself or a concomitant drug, exposure to the drug or the concomitant drug may decrease and consequently sufficient efficacy may not be obtained. As illustrated above, compounds (I) such as compounds 25, 27, 28, 30, 37, and the like. of Examples have lower CYP3A4-inducing activity than structural analogs and are thus have less potential to affect a concomitant drug. Therefore, compounds (I) are considered to be preferable.

Compound (I) or a pharmaceutically acceptable salt thereof can be used as it is or in various forms of pharmaceuticals depending on its pharmacological effect, the purpose of administration, and the like. A pharmaceutical composition of the present invention can be usually produced by homogeneously mixing an effective amount of compound (I) or a pharmaceutically acceptable salt thereof as an active ingredient with a pharmaceutically acceptable carrier. The carrier can be in a wide range of forms depending on the dosage form suitable for administration. Preferably, the pharmaceutical composition is in a dosage unit form suitable for oral administration or parenteral administration such as injection, and the like.

For preparation of tablets, for example, excipients such as lactose and mannitol; disintegrants such as starch; lubricants such as magnesium stearate; binders such as polyvinyl alcohol and hydroxypropyl cellulose; surfactants such as sucrose fatty acid ester and sorbitol fatty acid ester; and the like, can be used in a usual manner. Preferably, 1 to 200 mg of the active ingredient is contained per tablet.

For preparation of injections, water; saline; vegetable oils such as olive oil and peanut oil; solvents such as ethyl oleate and propylene glycol; solubilising agents such as sodium benroate, sodium salicylate and urethane; tonicity agents such as sodium chloride and glucose; preservatives such as phenol, cresol, p-hydroxybenzoic acid esters and chlorobutanol; anti-oxidants such as ascorbic acid and sodium pyrosulfite; and the like, can be used in a usual manner.

Compound (I) or a pharmaceutically acceptable salt thereof can be administered orally or parenterally (for example, injection, and the like). The effective dose and dose frequency vary depending on the dosage form, the age, body weight and condition of a patient, and the like, but in general, the daily dose is preferably 0.01 to 100 mg/kg.

Subjects to which compound (I) or a pharmaceutically acceptable salt thereof is administered are preferably patients with the above-described diseases associated with the production of kynurenine. Among these, patients with cancers (tumors), neurodegenerative diseases, infections, immune diseases, or the like are suitable, and patients with cancers (tumors) or the like are more suitable. These patients can be selected by a known diagnosis method. For prevention of the onset of these diseases, the compound can also be administered to mammals which may develop the diseases. Compound (I) or a pharmaceutically acceptable salt thereof or a composition containing said compound or salt thereof can be administered orally or parenterally to humans and non-human mammals (for example, mice, rats, hamsters, guinea pigs, rabbits, cats, dogs, pigs, cows, horses, sheeps, monkeys, and the like).

Hereinafter, the present invention will be illustrated in more detail by way of Examples and Reference Examples, but is not limited thereto.

In proton nuclear magnetic resonance spectroscopy ($^1$H-NMR), exchangeable hydrogens are sometimes not clearly observed depending on compounds and the measurement conditions. The multiplicity of the signals is denoted by notations which are generally employed. The symbol "for" represents an apparent broad signal.

The instrumental data of the compounds in the respective Reference Examples and Examples below were measured with the following devices:

$^1$H-NMR: JEOL JNM-EX270 (270 MHz) or JEOL JNM-AL300 (300 MHz) MS: JEOL SX-102AQQ (FAB method), JEOL JMS-DX303 (FAB method), Micromass Quattro (APCI method) or Micromass LCT (ESI, APCI method).

Unless otherwise noted, the symbol "%" regarding the concentration means "% by mass", and the ratio of solvents means the volume ratio of the solvents.

Each compound was named using ChemBioDraw ver. 11.0 (Cambridge soft).

The microwave synthesizer used was Discover (CEM Corporation).

Reference Example 2-1

N-(3-chloroquinoxalin-2-yl)propane-1-sulfonamide (Compound AA)

In DMSO were dissolved 2,3-dichloroquinoxaline (5.00 g, 25.1 mmol) and propane-1-sulfonamide (3.09 g, 25.1 mmol). Potassium carbonate (3.47 g, 25.1 mmol) was added and the mixture was stirred at 150° C. for 1 hour. A 1% aqueous acetic acid solution was added to the mixture and the mixture was stirred at room temperature for 3 hours. The precipitated solid was separated by filtration and the obtained solid was washed with water. The separated solid was then purified by slurrying in diisopropyl ether to give compound AA (6.01 g, 84% yield).

Reference Example 2-2

N-(3-chloroquinoxalin-2-yl)-N-((2-(trimethylsilyl)ethoxy) methyl)propane-1-sulfonamide (Compound AB)

Compound AA (1.22 g, 4.28 mmol) was dissolved in dichloromethane (12.0 mL). Diisopropylethylamine (1.5 mL, 8.6 mmol) and 2-(chloromethoxy)ethyltrimethylsilane (1.10 mL, 6.40 mmol) were added and the mixture was stirred at room temperature for 30 minutes. Water was added to the mixture and extraction with ethyl acetate was performed. The organic layer was washed with saturated brine, dried over anhydrous sodium sulfate, and filtered. The solvent was evaporated from the filtrate under reduced pressure. The residue was purified, by silica gel column chromatography (hexane/ethyl acetate=5/1) to give compound AB (1.68 g, 94% yield).

Reference Example 2-3

Step 1

2-Methoxyethanesulfonamide (Compound AC1)

In water (16 mL) was suspended 1-bromo-2-methoxyethane (2.00 mL, 21.3 mmol). Sodium sulfite (2.95 g, 23.4 mmol) was added and the mixture was refluxed for 24 hours. The solvent was evaporated from the mixture under reduced pressure. Chloroform was added to the residue and the residue was purified by slurrying to give a white solid (6.11 g). To the white solid were added thionyl chloride (15.5 mL, 213 mmol) and DMF (0.082 mL, 1.06 mmol) and the mixture was stirred at 100° C. for 3 hours. The solvent was evaporated from the mixture under reduced pressure. Chloroform was added and insoluble substance was filtered off. The solvent was evaporated from the filtrate under reduced pressure. A 25% aqueous ammonia solution (10 mL) was added to the resulting residue and the mixture was stirred at room temperature for 3 hours. The solvent was evaporated from the mixture under reduced pressure. Chloroform was added and the mixture was filtered. The solvent was evaporated from the filtrate under reduced pressure. The residue was purified by silica gel column chromatography (hexane/ethyl acetate=3/7) to give compound AC1 (1.36 g, 46% yield).

Step 2

N-(3-chloroquinoxalin-2-yl)-2-methoxyethanesulfonamide (Compound AC2)

According to Reference Example 2-1, compound AC2 (537 mg, 80% yield) was obtained from compound AC1 (308 mg, 2.21 mmol).

Step 3

N-(3-chloroquinoxalin-2-yl)-2-methoxy-N-((2-(trimethylsilyl)ethoxy)methyl)ethanesulfonamide (Compound AC)

According to Reference Example 2-2, compound AC (1.38 g, 96% yield) was obtained from compound AC2 (1.00 g, 3.31 mmol).

Reference Example 3-1

Step 1 tert-butyl 4-(hydroxymethyl)piperidin-1-carboxylate (Compound BA1)

Piperidin-4-ylmethanol (1.00 g, 8.68 mmol) was dissolved in dichloromethane (50.0 mL). Di-tert-butyl dicarbonate (2.4 mL, 10.4 mmol) was added and the mixture was stirred at room temperature for 2.5 hours. The solvent was evaporated from the mixture under reduced pressure to give the crude compound BA1.

Step 2 tert-butyl 4-formylpiperidine-1-carboxylate (Compound BA2)

Compound BA1 was dissolved in dichloromethane (50.0 mL). To this, 4-methylmorpholine N-oxide (2.03 g, 17.4 mmol) and tetrapropylammonium perruthenate (153 mg, 0.434 mmol) were added and the mixture was stirred at room temperature for 2 hours. The mixture was filtered and the solvent was evaporated from the filtrate under reduced pressure to give the crude compound BA2.

Step 3 tert-butyl 4-(2,2,2-trifluoro-1-hydroxyethyl)piperidin-1-carboxylate (Compound BA)

Compound BA2 was dissolved in THF (50.0 mL). (Trifluoromethyl)trimethylsilane (2.08 mL, 13.0 mmol) and tetrabutylammonium fluoride (1.0 mol/L solution in THF, 0.868 ml, 0.868 mmol) were added and the mixture was stirred at room temperature for 15 minutes. Additional tetrabutylammonium fluoride (1.0 mol/L solution in THF, 8.63 mL, 8.68 mmol) was added and the mixture was stirred at room temperature for 45 minutes. A saturated aqueous ammonium chloride solution was added to the mixture and extraction with ethyl acetate was performed. The organic layer was washed with saturated brine, dried over anhydrous sodium sulfate, and filtered. The solvent was evaporated from the filtrate under reduced pressure. The residue was purified by silica gel column chromatography (hexane/ethyl acetate=1/1) to give compound BA (1.47 g, 60% overall yield in 3 steps).

Reference Example 3-2

Step 1

2,2,2-trifluoro-1-(piperidin-4-yl)ethanol (Compound BB1)

Compound BA (255 g, 0.90 mmol) was dissolved in dichloromethane (4.0 mL). Trifluoroacetic acid (2.0 mL, 26.0 mmol) was added and the mixture was stirred at room temperature for 30 minutes. The solvent was evaporated from the mixture under reduced pressure. The residue was purified using Strata SCX [phenomenex Inc., particle size: 55 μm, pore size; 70 Å, sorbent mass: 5 g, volume: 20 mL Giga Tube, eluent: 2 mol/L ammonia/methanol solution] to give compound BB1 (156 mg, 95% yield).

Step 2

4-(2,2,2-trifluoro-1-hydroxyethyl)piperidin-1-carbonitrile (Compound BB)

Compound BB1 was dissolved in diethyl ether (10.0 mL). Sodium carbonate (269 mg, 2.54 mmol) and cyanobromide (117 mg, 1.10 mmol) were added and the mixture was stirred at room temperature for 15 hours. A sodium hypochlorite aqueous solution (Wako Pure Chemical Industries, Ltd., available chlorine concentration: 52 or more, 10.0 mL) was added to the mixture and extraction with ethyl acetate was performed. The organic layer was washed with saturated brine, dried over anhydrous sodium sulfate, and filtered. The solvent was evaporated from the filtrate under reduced pressure. The residue was purified by silica gel column chromatography (hexane/ethyl acetate=1/1) to give compound BB (1.47 g, 73% yield).

Reference Example 3-3

Step 1

2-bromo-5-(diethoxymethyl)pyridine (Compound BC1)

In ethanol (50 mL) was dissolved 6-bromonicotinaldehyde (6.00 g, 32.3 mmol). Triethyl orthoformate (10.74 mL, 64.5 mmol) and p-toluenesulfonic acid mono-hydrate (307 mg, 1.613 mmol) were added and the mixture was reflexed for 3 hours. The solvent was evaporated from the mixture under reduced pressure. A saturated sodium bicarbonate solution and water were added and extraction with ethyl acetate was performed. The organic layer was washed with saturated brine, dried over anhydrous sodium sulfate, and filtered. The solvent was evaporated from the filtrate under reduced pressure. The residue was purified by silica gel column chromatography (hexane/ethyl acetate=9/1) to give compound BC1 (7.60 g, 91% yield).

Step 2

5-(diethoxymethyl)picolinonitrile (Compound BC2)

In DMF (25 mL) were dissolved compound BC1 (7.60 q, 29.2 mmol), zinc cyanide (5.15 g, 43.8 mmol) and tetrakis (triphenylphosphine)palladium (6.75 g, 5.84 mmol). The mixture was stirred under nitrogen atmosphere at 80° C. for 15 hours. The mixture was filtered through Celite. Water was added to the resulting filtrate and extraction with ethyl acetate was performed. The organic layer was washed with saturated brine, dried over anhydrous magnesium sulfate, and filtered. The solvent was evaporated from the filtrate under reduced pressure. The residue was purified by silica gel column chromatography (hexane/ethyl acetate=9/1) to give compound BC2 (5.0 g, 83% yield).

Step 3

5-(diethoxymethyl)-N'-hydroxypicolinimidamide (Compound BC3)

Compound BC2 (2.3 g, 11.15 mmol) was dissolved in ethanol (10 mL). A 50% hydroxyl amine aqueous solution (3.32 mL, 55.8 mmol) was added and the mixture was stirred at room, temperature for 30 minutes. The solvent was evaporated from the mixture under reduced pressure. Water was added and extraction with ethyl acetate was performed. The organic layer was washed with saturated brine, dried over anhydrous magnesium sulfate, and filtered. The solvent was evaporated from the filtrate under reduced pressure to give compound BC3 as a white solid (2.4 g, 90% yield).

Step 4

(E)-N'-(cyclopropanecarbonyloxy)-5-(diethoxymethyl) picolinimidamide (Compound BC4)

Compound BC3 (400 mg, 1.672 mmol) was dissolved in dichloromethane (2 mL). Pyridine (0.20 mL, 2.508 mmol) and cyclopropanecarbonyl chloride (210 mg, 2.006 mmol) were added and the mixture was stirred at room temperature for 2 hours. A saturated sodium bicarbonate solution was added to the mixture and extraction with ethyl acetate was performed. The organic layer was washed with saturated brine, dried over anhydrous magnesium sulfate, and filtered. The solvent was evaporated from the filtrate under reduced pressure to give the crude compound BC4.

Step 5

5-cyclopropyl-3-(5-(diethoxymethyl)pyridin-2-yl)-1,2,4-oxadiazole (Compound BC5)

Acetonitrile (1 mL) was added to compound BC4. Tetrabutylammonium fluoride (1.0 mol/L solution in THF, 1.67 mL, 1.672 mmol) was added and the mixture was stirred at room temperature for 30 minutes. Saturated brine was added to the mixture and extraction with ethyl acetate was performed. The organic layer was dried over anhydrous magnesium sulfate and filtered. The solvent was evaporated from the filtrate under reduced pressure to give the crude compound BC5.

Step 6

6-(5-cyclopropy-1,2,4-oxadiazol-3-yl)nicotinaldehyde (Compound BC6)

Compound BC5 was dissolved in THF (2 ml). To this, 1 mol/L hydrochloric acid (2.0 mL) was added and the mixture was stirred at 50° C. for 2 hours. The mixture was neutralised with a saturated sodium bicarbonate solution and extraction with ethyl acetate was performed. The organic layer was washed with saturated brine, dried over anhydrous magnesium sulfate, and filtered. The solvent was evaporated from the filtrate under reduced pressure to give the crude product compound BC6.

Step 7

1-(6-(5-cyclopropyl-1,2,4-oxadiazol-3-yl)pyridin-3-yl)-2,2,2-trifluoroethanol (Compound BC)

According to Step 3 of Reference Example 3-1, compound BC (380 mg, 80% overall yield in 4 steps) was obtained from, compound BC6.

Reference Example 3-4

2,2,2-trifluoro-1-(6-(5-(methoxymethyl)-1,2,4-oxadiazol-3-yl)pyridin-3-yl)ethanol (Compound BD)

According to Steps 4 to 7 of Reference Example 3-3, compound BD (400 mg, 83% overall yield in 4 steps) was obtained from compound BC3 (400 mg, 1.672 mmol) and 2-methoxyacetyl chloride (218 mg, 2.006 mmol).

Reference Example 3-5

2,2,2-trifluoro-1-(6-(5-methyl-1,2,4-oxadiazol-3-yl) pyridin-3-yl)ethanol (Compound BE)

According to Steps 4 to 7 of Reference Example 3-3, compound BE (738 mg, 68% overall yield in 4 steps) was obtained from compound BC3 (1.11 g, 4.64 mmol) and acetyl chloride (1.65 mL, 23.2 mmol).

Reference Example 3-6

Step 1

5-(diethoxymethyl)picolinaldehyde (Compound BF1)

To toluene (3 mL) were added dropwise, at −78° C., n-butyllithium (2.6 mol/L solution in n-hexane, 0.94 mL, 2.43 mmol) and a solution of compound BC1 (575 mg, 2.21 mmol) in toluene (2 mL). The mixture was stirred at −78° C. for 30 minutes. To the resulting suspension, THF (2 mL) was added and the mixture was stirred at −78° C. for 30 minutes. DMF (0.51 mL, 6.63 mmol) was added and the mixture was stirred for 30 minutes allowing the temperature to gradually rise to room temperature. A saturated aqueous ammonium chloride solution and water were added to the mixture and extraction with ethyl acetate was performed. The organic layer was washed with saturated brine, dried over anhydrous sodium sulfate, and filtered. The solvent was evaporated from the filtrate under reduced pressure. The residue was purified by silica gel column chromatography (hexane/ethyl acetate=9/1) to give compound BF1 (149 mg, 32% yield).

Step 2

5-(5-(diethoxymethyl)pyridin-2-yl)oxazole (Compound BF2)

Compound BF1 (148 mg, 0.707 mmol) was dissolved in methanol (5 mL). Toluene-4-sulfonylmethylisocyanide (345 mg, 1.77 mmol) and potassium carbonate (244 mg, 1.77 mmol) were added and the mixture was stirred at room temperature for 8 hours. Water was added to the mixture and extraction with ethyl acetate was performed. The organic layer was washed with saturated brine, dried over anhydrous sodium sulfate, and filtered. The solvent was evaporated from the filtrate under reduced pressure. The residue was purified, by silica gel column chromatography (hexane/ethyl acetate=7/3) to give compound BF2 (161 mg, 92% yield).

Step 3

6-(Oxazol-5-yl)nicotinaldehyde (Compound BF3)

According to Step 6 of Reference Example 3-3, compound BF3 (98.1 mg, 88% yield) was obtained from compound BF2 (160 mg, 0.647 mmol).

Step 4

2,2,2-trifluoro-1-(6-(oxazol-5-yl)pyridin-3-yl)ethanol (Compound BF)

According to Step 3 of Reference Example 3-1, compound BF (124 mg, 90% yield) was obtained from compound BF3 (98.2 mg, 0.564 mmol).

Reference Example 3-7

Step 1

1-(2-bromothiazol-5-yl)-2,2,2-trifluoroethanol (Compound BG1)

According to Step 3 of Reference Example 3-1, compound BG1 (413 mg, 25%) was obtained from 2-bromothiazole-5-carbaldehyde (1.20 g, 6.25 mmol).

Step 2

2-bromo-5-(1-(tert-butyldimethylsilyloxy)-2,2,2-trifluoroethyl)thiazole (Compound BG2)

Compound BG1 (413 mg, 1.58 mmol) was dissolved in dichloromethane (4 mL). Triethylamine (1.63 mL, 11.8 mmol) and tert-butyldimethylsilyl trifluoromethanesulfonate (1.09 mL, 4.73 mmol) were added under ice-cooling and the mixture was stirred at room temperature for 12 hours. Water was added to the mixture and extraction with ethyl acetate was performed. The organic layer was dried over anhydrous magnesium sulfate and filtered. The solvent was evaporated from the filtrate under reduced pressure. The residue was purified by silica gel column chromatography (hexane/ethyl acetate=5/1) to give compound BG2 (524 mg, 88%).

Step 3

1-(5-(1-(tert-butyldimethylsilyloxy)-2,2,2-trifluoroethyl) thiazol-2-yl)ethanone (Compound BG3)

Compound BG2 (515 mg, 1.37 mmol) was dissolved in THF (5 mL). n-butyllithium (1.65 mol/L solution in n-hexane, 1.24 mL, 2.05 mmol) was added dropwise at −5° C. and the mixture was stirred at −78° C. for 30 minutes. A solution of N-methoxy-N-methylacetamide (1.38 mL, 13.7 mmol) in THF (1 mL) was added to the mixture and the mixture was stirred at −78° C. for 2 hours. A saturated aqueous ammonium chloride solution and water were added to the mixture and extraction with ethyl acetate was performed. The organic layer was dried over anhydrous magnesium sulfate and filtered. The solvent was evaporated from the filtrate under reduced pressure. The residue was purified by silica gel column chromatography (hexane/ethyl acetate=4/1) to give compound BG3 (437 mg, 94%).

Step 4

1-(5-(2,2,2-trifluoro-1-hydroxyethyl)thiazol-2-yl) ethanone (Compound BG)

Compound BG3 (356 mg, 1.05 mmol) was dissolved in THF (3 mL). Acetic acid (0.072 mL, 1.26 mmol) and tetrabutylammonium fluoride (1.0 mol/L solution in THF, 1.26 ml, 1.26 mmol) were added and the mixture was stirred at room temperature for 1 hour. A saturated aqueous sodium carbonate solution was added to the mixture and extraction with ethyl acetate was performed. The organic layer was washed with a saturated aqueous ammonium chloride solution, dried over anhydrous magnesium, sulfate, and filtered. The solvent was evaporated from the filtrate under reduced pressure. The residue was purified by silica gel column chromatography (hexane/ethyl acetate=1/1) to give compound BG (214 ng, 91%).

Reference Example 4

Step 1 tert-butyl 4-(2,2,2-trifluoro-1-(3-(propylsulfonamido)quinoxalin-2-yloxy)ethyl)piperidine-1-carboxylate (Compound CA1)

Compound AA (142 mg, 0.498 mmol) and compound BA (94.0 mg, 0.332 mmol) were dissolved in THF (2.5 mL). To this, 60% sodium hydride (in oil, 59.7 mg, 1.49 mmol) was added and the mixture was stirred at 50° C. for 2 hours. A saturated aqueous ammonium chloride solution and wafer were added to the mixture and extraction with ethyl acetate was performed. The organic layer was washed with saturated brine, dried over anhydrous sodium sulfate, and filtered. The solvent was evaporated from the filtrate under reduced pressure. The residue was purified by silica gel column chromatography (hexane/ethyl acetate=1/1) to give compound CA1 (145 mg, 82% yield).

Step 2

N-(3-(2,2,2-trifluoro-1-(piperidin-4-yl)ethoxy)quinoxalin-2-yl)propane-1-sulfonamide hydrochloride (Compound CA2)

Compound CA1 (140 mg, 0.263 mmol) was dissolved in ethyl acetate (1 mL). A 4 mol/L hydrogen chloride/ethyl acetate solution (1 mL) was added and the mixture was stirred at 50° C. for 2 hours. The solvent was evaporated from the mixture under reduced pressure. Diisopropyl ether was added to the residue and the mixture was purified by slurrying to give compound CA2 (83.5 mg, 68%. yield).

Reference Example 5

2-bromo-N,N-dimethylnicotinamide (Compound DA1)

In DMF (20 mL) was dissolved 2-bromonicotinic acid (2.00 g, 9.90 mmol). To this were added triethylamine (4.14 mL, 29.7 mmol), dimethylamine (2 mol/L solution in THF, 9.90 mL, 19.8 mmol), 1-hydroxybenzotriazole monohydrate (2.27 g, 14.85 mmol), and 1-(3-dimethylaminopropyl)-3-ethylcarbodiimide hydrochloride (2.85 g, 14.85 mmol), and the mixture was stirred at room temperature for 12 hours. A saturated aqueous ammonium chloride solution was added to the mixture and extraction with ethyl acetate was performed. The organic layer was washed with saturated brine, dried over anhydrous sodium sulfate, and filtered. The solvent was evaporated from the filtrate under-reduced pressure. The residue was purified by silica gel column chromatography (ethyl acetate) to give compound DA1 (1.40 g, 60% yield).

Reference Example 6

Step 1

N-(3-(1-(1-cyanopiperidin-4-yl)-2,2,2-trifluoroethoxy) quinoxalin-2-yl)propane-1-sulfonamide (Compound EA1)

According to Step 1 of Reference Example 4, compound EA1 (270 mg, 100% yield) was obtained from compound AA (247 mg, 0.865 mmol) and compound BB (120 mg, 0.576 mmol).

Step 2

N-(3-(1-cyanopiperidin-4-yl)-2,2,2-trifluoroethoxy)
quinoxalin-2-yl)-N-((2-trimethylsilyl)ethoxy)methyl)
propane-1-sulfonamide (Compound EA2)

Compound EA1 (115 mg, 0.251 mmol) was dissolved in dichloromethane (3 mL). N,N-diisopropylethylamine (0.066 mL, 0.377 mmol) and 2-(chloromethoxy)ethyltrimethylsilane (0.054 mL, 0.302 mmol) were added and the mixture was stirred at room temperature for 2 hours. A saturated aqueous ammonium, chloride solution and water were added to the mixture and extraction with chloroform was performed. The organic layer was dried over anhydrous sodium sulfate and filtered. The solvent was evaporated from the filtrate under reduced pressure. The residue was purified by silica gel column chromatography (hexane/ethyl acetate=1/1) to give compound EA2 (134 mg, 91%).

Step 3

N-(3-(1-(1-(2H-tetrazol-5-yl)piperidin-4-yl)-2,2,2-
trifluoroethoxy)quinoxalin-2-yl)-N-((2-(trimethylsilyl) ethoxy)methyl)propane-1-sulfonamide (Compound EA3)

Compound EA2 (80 mg, 0.136 mmol) was dissolved in toluene (3 mL). Trimethylsilyl azide (157 mg, 1.36 mmol) and dibutyltin oxide (16.9 mg, 0.063 mmol) were added and the mixture was stirred at 80° C. for 2 hours. Water was added to the mixture and extraction with chloroform was performed. The organic layer was dried over anhydrous sodium sulfate and filtered. The solvent was evaporated from the filtrate under reduced pressure to give the crude compound EA3.

Step 4

N-(3-(2,2,2-trifluoro-1-(1-(2-methyl-2H-tetrazol-5-
yl) piperidin-4-yl)ethoxy)quinoxalin-2-yl)-N-((2-
(trimethylsilyl)ethoxy)methyl)propane-1-sulfonamide (Compound EA4)

N-(3-(2,2,2-trifluoro-1-(1-(1-methyl-1H-tetrazol-5-
yl) piperidin-4-yl)ethoxy)quinoxalin-2-yl)-N-((2-
(trimethylsilyl)ethoxy)methyl)propane-1-sulfonamide (Compound EA5)

The total amount of compound EA3 obtained in Step 3 was dissolved in DMF (3 mL). Methyl 4-methylbenzenesulfonate (0.031 mL, 0.204 mmol) and potassium carbonate (37.6 mg, 0.272 mmol) were added and the mixture was stirred at 50° C. for 1.5 hours. Water was added to the mixture and extraction with ethyl acetate was performed. The organic layer was washed with saturated brine, dried over anhydrous sodium sulfate, and filtered. The solvent was evaporated from the filtrate under reduced pressure. The residue was purified by silica gel column chromatography (hexane/ethyl acetate=1/1) to give compound EA4 (68.4 mg, 78% overall yield in 2 steps) and compound. EA5 (11.0 mg, 13% overall yield in 2 steps).

Reference Example 7

N-(3-(1-(6-(5-cyclopropyl-1,2,4-oxadiazol-3-yl)pyridin-3-yl)-2,2,2-trifluoroethoxy)quinoxalin-2-yl)-2-
methoxy-N-(2-(trimethylsilyl)methyl)ethane-
sulfonamide (Compound FA1)

According to Step 1 of Reference Example 4, compound FA1 (200 mg, 56% yield) was obtained from compound AC (250 mg, 0.578 mmol) and compound BC (150 mg, 0.526 mmol).

Reference Example 8

2-methoxy-N-(3-(2,2,2-trifluoro-1-(6-(5-(methoxymethyl)-1,2,4-oxadiazol-3-yl) pyridin-3-yl)ethoxy)
quinoxalin-2-yl)-N-((2-(trimethylsilyl)ethoxy)methyl)ethanesulfonamide (Compound GA1)

According to Step 1 of Reference Example 4, compound GA1 (370 mg, 98% yield) was obtained from compound AC (263 mg, 0.609 mmol) and compound BD (160 mg, 0.553 mmol).

Reference Example 9

N-(3-(1-(6-(5-cyclopropyl-1,2,4-oxadiazol-3-yl)pyridin-3-yl)-2,2,2-trifluoroethoxy)quinoxalin-2-yl)-2-
methoxy-N-((2-(trimethylsilyl)ethoxy)methyl)propane-1-sulfonamide (Compound HA1)

According to Step 1 of Reference Example 4, compound HA1 (240 mg, 79% yield) was obtained from compound AB (209 mg, 0.501 mmol) and compound BC (130 mg, 0.456 mmol).

Reference Example 10

N-(3-(2,2,2-trifluoro-1-(6-(5-(methoxymethyl)-1,2,4-
oxadiazol-3-yl)pyridin-3-yl)ethoxy)quinoxalin-2-yl)-
N-((2-(trimethylsilyl)ethoxy)methyl)propane-1-sulfonamide (Compound IA1)

According to Step 1 of Reference Example 4, compound IA1 (260 mg, 70% yield) was obtained from, compound AB (253 mg, 0.609 mmol) and compound BD (160 mg, 0.553 mmol).

Reference Example 11

2-methoxy-N-(3-(2,2,2-trifluoro-1-(6-(5-methyl-1,2,
4-oxadiazol-3-yl) pyridin-3-yl) ethoxy)quinoxalin-2-
yl)-N-((2-(trimethylsilyl)ethoxy)methyl)ethane-
sulfonamide (Compound JA1)

According to Step 1 of Reference Example 4, compound JA1 (1.14 mg, 90% yield) was obtained from compound AC (92.0 mg, 0.212 mmol) and compound BE (50.0 mg, 0.193 mmol).

Reference Example 12

Step 1

N-(3-(2,2,2-trifluoro-1-(6-(5-methyl-1,2,4-oxadiazol-3-yl) pyridin-3-yl)ethoxy)quinoxalin-2-yl)-N-((2-(trimethylsilyl) ethoxy)methyl)propane-1-sulfonamide (Compound KA1)

According to Step 1 of Reference Example 4, compound KA1 (1.01 g, 84% yield) was obtained from compound AB (936 mg, 2.25 mmol) and compound BE (530 mg, 2.05 mmol).

Step 2

N-(3-(2,2,2-trifluoro-1-(6-(5-methyl-1,2,4-oxadiaxol-3-yl) pyridin-3-yl)ethoxy)quinoxalin-2-yl)propane-1-sulfonamide (Compound KA2)

According to Example 12, compound KA2 (559 mg, 70%) was obtained from compound KA1 (1.00 g, 1.57 mmol).
ESIMS m/z: 509 (M+H)$^+$.

Reference Example 13

Step 1

2-methoxy-N-(3-(2,2,2-trifluoro-1-(6-(oxazol-5-yl) pyridin-3-yl)ethoxy)quinoxalin-2-yl)-N-((2-(trimethylsilyl)ethoxy) methyl)ethanesulfonamide (Compound LA1)

According to Step 1 of Reference Example 4, compound LA1 (2.52 g, 96%) was obtained from compound AC (1.95 g, 4.51 mmol) and compound BF (1.00 g, 4.10 mmol).

Step 2

2-methoxy-N-(3-(2,2,2-trifluoro-1-(6-(oxasol-5-yl) pyridin-3-yl)ethoxy)quinoxalin-2-yl)ethanesulfonamide (Compound LA2)

According to Example 12, compound LA2 (1.73 g, 86%) was obtained from compound LA1 (2.52 g, 3.94 mmol).

Reference Example 14

Step 1

N-(3-(1-(2-acetylthiazol-5-yl)-2,2,2-trifluoroethoxy) quinoxalin-2-yl)-N-((2-(trimethylsilyl)ethoxy)methyl) propane-1-sulfonamide (Compound MA1)

According to Step 1 of Reference Example 4, compound MA1 (55.8 mg, 40%) was obtained from compound AB (105 mg, 0.253 mmol) and compound BG (51.7 mg, 0.230 mmol).

Step 2

N-(3-(1-(2-acetylthiazol-5-yl)-2,2,2-trifluoroethoxy) quinoxalin-2-yl)propane-1-sulfonamide (Compound MA2)

According to Example 12, compound MA2 (43.2 mg, 99%) was obtained from compound MA1 (55.8 mg, 0.092 mmol).

Example 1

N,N-dimethyl-2-(4-(2,2,2-trifluoro-1-(3-(propylsulfonamido) quinoxalin-2-yloxy)ethyl)piperidin-1-yl) isonicotinamide (Compound 1)

Compound CA2 (50.0 mg, 0.107 mmol) was dissolved in toluene (2 mL). To this were added 2-bromo-N,N-dimethyl-isonicotinamide (48.9 mg, 0.213 mmol), tris(dibenzylideneacetone)dipalladium (19.5 mg, 0.021 mmol), 4,5-bis(diphenylphosphino)-9,9-dimethylxanthene (24.7 mg, 0.043 mmol) and cesium carbonate (174 mg, 0.553 mmol), and the mixture was stirred at 100° C. for 15 hours. A saturated aqueous ammonium chloride solution and water were added to the mixture and extraction with ethyl acetate was performed. The organic layer was dried over anhydrous sodium sulfate and filtered. The solvent was evaporated from the filtrate under reduced pressure. The residue was purified by silica gel column chromatography (hexane/ethyl acetate=1/1) to give compound 1 (6.7 mg, 10% yield).
ESIMS m/z: 581 (M+H)$^+$.

Example 2

N,N-dimethyl-2-(4-(2,2,2-trifluoro-1-(3-(propylsulfonamido) quinoxalin-2-yloxy)ethyl)piperidin-1-yl) nicotinamide (Compound 2)

According to Example 1, compound 2 (16.5 mg, 27%) was obtained from compound CA2 (50.0 mg, 0.107 mmol) and compound DA1 (48.9 mg, 0.213 mmol).
ESIMS m/s: 581 (M+H)$^+$.

Example 3

N,N-dimethyl-6-(4-(2,2,2-trifluoro-1-(3-(propylsulfonamido) quinoxalin-2-yloxy)ethyl)piperidin-1-yl) picolinamide (Compound 3)

According to Example 1, compound 3 (7.9 mg, 13% yield) was obtained from compound CA2 (50.0 mg, 0.107 mmol) and 6-bromo-N,N-dimethylpicolinamide (48.9 mg, 0.213 mmol).
ESIMS m/z: 581 (M+H)$^+$.

Example 4

N-(3-(1-(1-(6-cyanopyridin-3-yl)piperidin-4-yl)-2,2,2-trifluoroethoxy)quinoxalin-2-yl)propane-1-sulfonamido (Compound 4)

According to Example 1, compound 4 (44.4 mg, 78% yield) was obtained from compound CA2 (50.0 mg, 0.107 mmol) and 5-bromopicolinonitrile (39.0 mg, 0.213 mmol).
ESIMS m/z: 535 (M+H)$^+$.

Example 5

5-(4-(2,2,2-trifluoro-1-(3-(propylsulfonamido)quinoxalin-2-yloxy)ethyl)piperidin-1-yl)picolinamide (Compound 5)

Compound 4 (44.4 mg, 0.083 mmol) was dissolved in DMSO (2 mL). Potassium carbonate (34.4 mg, 0.249 mmol) and a hydrogen peroxide solution (31 wt %, 0.8 mL, 8.09 mmol) were added and the mixture was stirred at room temperature for 3 hours. A saturated aqueous ammonium chloride solution and water were added to the mixture and extraction with ethyl acetate was performed. The organic layer was dried over anhydrous sodium sulfate and filtered. The solvent was evaporated from the filtrate under reduced pressure. The residue was purified by silica gel column chromatography (ethyl acetate) to give compound 5 (25.0 mg, 48%).

ESIMS m/z: 553 (M+H)$^+$.

Example 6

N-(3-(1-(1-(4-cyanopyridin-2-yl)piperidin-4-yl)-2,2, 2-trifluoroethoxy)quinoxalin-2-yl)propane-1-sulfonamide (Compound 6)

Compound CA2 (31.6 mg, 0.067 mmol) was dissolved in ethanol (1 mL). To this, 2-chloroisonicotinonitrile (16.7 mg, 0.135 mmol) and triethylamine (0.047 mL, 0.337 mmol) were added and the mixture was stirred in a microwave synthesizer at 250 W at 120° C. for 1.5 hours. A saturated aqueous ammonium chloride solution and water were added to the mixture and extraction with ethyl acetate was performed. The organic layer was dried over anhydrous sodium sulfate and filtered. The solvent was evaporated from the filtrate under reduced pressure. The residue was purified by silica gel column chromatography (hexane/ethyl acetate=3/1) to give compound 6 (2.4 mg, 6.7%).

ESIMS m/z: 535 (M+H)$^+$.

Example 7

N-(3-(1-(1-(5-cyanopyridin-3-yl)piperidin-4-yl)-2,2, 2-trifluoroethoxy)quinoxalin-2-yl)propane-1-sulfonamide (Compound 7)

According to Example 1, compound 7 (37.7 mg, 66% yield) was obtained from compound CA2 (50.0 mg, 0.107 mmol) and 5-bromonicotinonitrile (39.0 mg, 0.213 mmol).

ESIMS m/z: 535 (M+H)$^+$.

Example 8

N,N-dimethyl-6-(4-(2,2,2-trifluoro-1-(3-(propylsulfonamido) quinoxalin-2-yloxy)ethyl)piperidin-1-yl) nicotinamide (Compound 8)

According to Example 6, compound 8 (6.7 mg, 5.4% yield) was obtained from compound CA2 (100 mg, 0.213 mmol) and 6-chloro-N,N-dimethylnicotinamide (79.0 mg, 0.427 mmol).

ESIMS m/z: 581 (M+H)$^+$.

Example 9

N-(3-(1-(1-(3-cyanopyridin-2-yl)piperidin-4-yl)-2,2, 2-trifluoroethoxy)quinoxalin-2-yl)propane-1-sulfonamide (Compound 9)

According to Example 6, compound 9 (84.7 mg, 74% yield) was obtained from compound CA2 (100 mg, 0.213 mmol) and 2-chloronicotinonitrile (0.059 g, 0.427 mmol).

ESIMS m/z: 535 (M+H)$^+$.

Example 10

2-(4-(2,2,2-trifluoro-1-(3-(propylsulfonamido)quinoxalin-2-yloxy)ethyl)piperidin-1-yl)nicotinamide (Compound 10)

According to Example 5, compound 10 (22.2 mg, 86% yield) was obtained from compound 9 (25.0 mg, 0.047 mmol).

ESIMS m/z: 553 (M+H)$^+$.

Example 11

N-(3-(2,2,2-trifluoro-1-(1-((2-methyl-2H-tetrazol-5-yl) piperidin-4-yl)ethoxy)quinoxalin-2-yl)propane-1-sulfonamide (Compound 11)

Compound EA4 (63.0 mg, 0.105 mmol) was dissolved in dichloromethane (2 mL). Trifluoroacetic acid (0.5 mL, 6.49 mmol) was added and the mixture was stirred at room temperature for 10 minutes. A saturated sodium bicarbonate solution was added to the mixture and extraction with chloroform was performed. The organic layer was dried over anhydrous sodium sulfate and filtered. The solvent was evaporated from the filtrate under reduced pressure. The residue was purified by silica gel column chromatography (hexane/ethyl acetate=1/1) to give compound 11 (52.5 mg, 97% yield).

ESIMS m/z: 515 (M+H)$^+$.

Example 12

N-(3-(2,2,2-trifluoro-1-(1-(1-methyl-1H-tetrazol-5-yl) piperidin-4-yl)ethoxy)quinoxalin-2-yl)propane-1-sulfonamide (Compound 12)

According to Example 11, compound 12 (8.5 mg, 97% yield) was obtained from compound EA5 (11.0 mg, 0.017 mmol).

ESIMS m/z: 515 (M+H)$^+$.

Example 13

N-(3-(2,2,2-trifluoro-1-(1-(pyrazin-2-yl)piperidin-4-yl) ethoxy)quinoxalin-2-yl)propane-1-sulfonamide (Compound 13)

According to Example 6, compound 13 (6.5 mg, 11%) was obtained from compound CA2 (52.8 mg, 0.113 mmol) and 2-chloro pyrazine (0.020 mL, 0.225 mmol).

ESIMS m/z: 511 (M+H)$^+$.

Example 14

N-(3-(2,2,2-trifluoro-1-(1-(pyrimidin-5-yl)piperidin-4-yl) ethoxy)quinoxalin-2-yl)propane-1-sulfonamide (Compound 14)

According to Example 1, compound 14 (9.5 mg, 19%) was obtained from compound CA2 (46.0 mg, 0.098 mmol) and 5-bromopyrimidine (31.2 mg, 0.196 mmol).

ESIMS m/z: 511 (M+H)$^+$.

Example 15

N-(3-(1-(1-(5-cyanopyridin-2-yl)piperidin-4-yl)-2,2,2-trifluoroethoxy)quinoxalin-2-yl)propane-1-sulfonamide (Compound 15)

According to Example 6, compound 15 (59.1 mg, 90%) was obtained from compound CA2 (57.3 mg, 0.122 mmol) and 6-chloronicotinonitrile (3.39 mg, 0.244 mmol).
ESIMS m/z: 535 (M+H)$^+$.

Example 16

N-(3-(1-(1-(2-cyanopyridin-4-yl)piperidin-4-yl)-2,2,2-trifluoroethoxy)quinoxalin-2-yl)propane-1-sulfonamide (Compound 16)

According to Example 6, compound 16 (19.8 mg, 33%) was obtained from compound CA2 (53.4 mg, 0.114 mmol) and 4-chloropicolinonitrile (31.6 mg, 0.228 mmol).
ESIMS m/z: 535 (M+H)$^+$.

Example 17

N-(3-(1-(1-(3-cyanopyridin-4-yl)piperidin-4-yl)-2,2,2-trifluoroethoxy)quinoxalin-2-yl)propane-1-sulfonamide (Compound 17)

According to Example 6, compound 17 (60.1 mg, 84%) was obtained from compound CA2 (62.4 mg, 0.133 mmol) and 4-chloronicotinonitrile (36.9 mg, 0.266 mmol).
ESIMS m/z: 535 (M+H)$^+$.

Example 18

N-(3-(2,2,2-trifluoro-1-(1-(thiazol-2-yl)piperidin-4-yl) ethoxy)quinoxalin-2-yl)propane-1-sulfonamide (Compound 18)

According to Example 1, compound 18 (6.5 mg, 18%) was obtained from compound CA2 (32.2 mg, 0.069 mmol) and 2-bromothiazol (22.5 mg, 0.137 mmol).
ESIMS m/z: 516 (M+H)$^+$.

Example 19

6-(4-(2,2,2-trifluoro-1-(3-(propylsulfonamido)quinoxalin-2-yloxy)ethyl)piperidin-1-yl)nicotinamide (Compound 19)

According to Example 6, compound 19 (12.3 mg, 17%) was obtained from compound CA2 (62.3 mg, 0.133 mmol) and 6-chloronicotinamide (41.6 mg, 0.266 mmol).
ESIMS m/z: 553 (M+H)$^+$.

Example 20

N-(3-(2,2,2-trifluoro-1-(1-(pyridin-2-yl)piperidin-4-yl) ethoxy)quinoxalin-2-yl)propane-1-sulfonamide (Compound 20)

According to Example 1, compound 20 (27.1 mg, 42%) was obtained from compound CA2 (59.3 mg, 0.126 mmol) and 2-iodopyridine (0.026 mL, 0.253 mmol).
ESIMS m/z: 510 (M+H)$^+$.

Example 21

N-(3-(2,2,2-trifluoro-1-(1-(pyridin-3-yl)piperidin-4-yl) ethoxy)quinoxalin-2-yl)propane-1-sulfonamide (Compound 21)

According to Example 1, compound 21 (11.3 mg, 35%) was obtained from compound CA2 (30.0 mg, 0.064 mmol) and 3-iodopyridine (26.2 mg, 0.128 mmol).
ESIMS m/z: 510 (M+H)$^+$.

Example 22

N-(3-(2,2,2-trifluoro-1-(1-(pyridin-4-yl)piperidin-4-yl) ethoxy)quinoxalin-2-yl)propane-1-sulfonamide (Compound 22)

According to Example 6, compound 22 (20.1 mg, 28%) was obtained from compound CA2 (65.7 mg, 0.140 mmol) and 4-chloropyridine hydrochloride (31.5 mg, 0.210 mmol).
ESIMS m/z: 510 (M+H)$^+$.

Example 23

N-(3-(1-(6-(5-cyclopropyl-1,2,4-oxadiazol-3-yl)pyridin-3-yl)-2,2,2-trifluoroethoxy)quinoxalin-2-yl)-2-methoxyethanesulfonamide (Compound 23)

According to Example 11, compound 23 (48 mg, 33% yield) was obtained from compound FA1 (180 mg, 0.264 mmol).
ESIMS m/z: 551 (M+H)$^+$.

Example 24

2-methoxy-N-(3-(2,2,2-trifluoro-1-(6-(5-(methoxymethyl)-1,2,4-oxadiazol-3-yl)pyridin-3-yl)ethoxy) quinoxalin-2-yl) ethanesulfonamide (Compound 24)

According to Example 11, compound 24 (120 mg, 91% yield) was obtained from compound GA1 (175 mg, 0.256 mmol).
ESIMS m/z: 555 (M+H)$^+$.

Example 25

N-(3-(1-(6-(5-cyclopropyl-1,2,4-oxadiazol-3-yl)pyridin-3-yl)-2,2,2-trifluoroethoxy)quinoxalin-2-yl)propane-1-sulfonamide (Compound 25)

According to Example 11, compound 25 (92 mg, 64% yield) was obtained from compound HA1 (180 mg, 0.264 mmol).
ESIMS m/z: 535 (M+H)$^+$.

Example 26

N-(3-(2,2,2-trifluoro-1-(6-(5-(methoxymethyl)-1,2,4-oxadiazol-3-yl)pyridin-3-yl)ethoxy)quinoxalin-2-yl) propane-1-sulfonamide (Compound 26)

According to Example 11, compound 26 (120 mg, 85% yield) was obtained from compound IA1 (175 mg, 0.262 mmol).
ESIMS m/z: 539 (M+H)$^+$.

Example 27

2-methoxy-N-(3-(2,2,2-trifluoro-1-(6-(5-methyl-1,2,4-oxadiazol-3-yl)pyridin-3-yl)ethoxy)quinoxalin-2-yl) ethanesulfonamide (Compound 27)

According to Example 11, compound 27 (78.9 mg, 86% yield) was obtained from compound JA1 (114 mg, 0.174 mmol).
ESIMS m/z: 525 (M+H)$^+$.

Example 28

(R)-N-(3-(2,2,2-trifluoro-1-(6-(5-methyl-1,2,4-oxadiaxol-3-yl)pyridin-3-yl)ethoxy)quinoxalin-2-yl) propane-1-sulfonamide (Compound 28)

(S)-N-(3-(2,2,2-trifluoro-1-(6-(5-methyl-1,2,4-oxadiazol-3-yl)pyridin-3-yl)ethoxy)quinoxalin-2-yl) propane-1-sulfonamide (Compound 29)

Compound KA2 (420 mg) was resolved into enantiomers, compound 28 (210 mg) and compound 29 (210 mg), by preparative high performance liquid chromatography [CHIRALCEL (registered trademark) OJ-H (Daicel Chemical Industries), particle diameter 5 μm, 2 cm (internal diameter)×25 cm (length), methanol/acetonitrile/acetic acid=95/5/0.1 (v/v), flow rate 5.7 mL/min, column oven temperature 40° C., detection wavelength 267 nm]. The compound with a retention time of 25.7 minutes was designated as compound 28 and the compound with a retention time of 19.3 minutes was designated as compound 29.
Compound 28: ESIMS m/z: 509 (M+H)$^+$.
Compound 29: ESIMS m/z: 509 (M+H)$^+$.

Example 29

(R)-2-methoxy-N-(3-(2,2,2-trifluoro-1-(6-(oxazol-5-yl) pyridin-3-yl)ethoxy)quinoxalin-2-yl)ethanesulfonamide (Compound 30)

(S)-2-methoxy-N-(3-(2,2,2-trifluoro-1-(5-(oxazol-5-yl) pyridin-3-yl)ethoxy)quinoxalin-2-yl)ethanesulfonamide (Compound 31)

In the same manner as in Example 28, compound LA2 (940 mg) was resolved into enantiomeric, compound 30 (480 mg) and compound 31 (460 mg), by preparative high performance liquid chromatography [CHIRALPAC (registered trademark) IC (Daicel Chemical Industries), particle diameter 5 μm, 2 cm (internal diameter)×25 cm (length), chloroform/ethanol/acetic acid=98/2/0.05 (v/v), flow rate 6 mL/min, column oven temperature 40° C., detection wavelength 277 nm]. The compound with a retention time of 15.8 minutes was designated as compound 30 and the compound with a retention time of 18.3 minutes was designated as compound 31.
Compound 30: ESIMS m/z: 510 (M+H)$^+$.
Compound 31: ESIMS m/z: 510 (M+H)$^+$.

Example 30

(S)-N-(3-(1-(2-acetylthiazol-5-yl)-2,2,2-trifluoroethoxy) quinoxalin-2-yl)propane-1-sulfonamide (Compound 32)

(R)-N-(3-(1-(2-acetylthiazol-5-yl)-2,2,2-trifluoroethoxy) quinoxalin-2-yl)propane-1-sulfonamide (Compound 33)

In the same manner as in Example 28, compound MA2 (500 mg) was resolved into enantiomers, compound 32 (250 mg) and compound 33 (250 mg), by preparative high performance liquid chromatography [CHIRALPAC IC (Daicel Chemical Industries), particle diameter 5 μm, 2 cm (internal diameter)×25 cm (length), n-hexane/2-propanol/ethanol=75/20/5 (v/v), flow rate 5.7 mL/min, column oven temperature 40° C., detection wavelength 285 nm]. The compound with a retention time of 29.7 minutes was designated as compound 32 and the compound with a retention time of 34.4 minutes was designated as compound 33.
Compound 32: ESIMS m/z: 475 (M+H)$^+$.
Compound 33: ESIMS m/z: 475 (M+H)$^+$.

Example 11

(R)-5-(4-(2,2,2-trifluoro-1-(3-(propylsulfonamido) quinoxalin-2-yloxy)ethyl)piperidin-1-yl)picolinamide (Compound 34)

(S)-5-(4-(2,2,2-trifluoro-1-(3-(propylsulfonamido) quinoxalin-2-yloxy)ethyl)piperidin-1-yl)picolinamide (Compound 35)

In the same manner as in Example 28, compound 5 (430 mg) was resolved into enantiomers, compound 34 (210 mg) and compound 35 (220 mg), by preparative high performance liquid chromatography [CHIRALCEL OZ-H (Daicel Chemical Industries), particle diameter 5 μm, 5 cm (internal diameter)×25 cm (length), methanol/acetic acid=100/0.1 (v/v), flow rate 35 mL/min, column oven temperature 40° C., detection wavelength 246 nm]. The compound with a retention time of 33.5 minutes was designated as compound 34 and the compound with a retention time of 53.4 minutes was designated as compound 35.
Compound 34: ESIMS m/z: 553 (M+H)$^+$.
Compound 35: ESIMS m/z: 553 (M+H)$^+$.

Example 32

(S)-N-(3-(1-(6-(5-cyclopropyl-1,2,4-oxadiazol-3-yl) pyridin-8-yl)-2,2,2-trifluoroethoxy)quinoxalin-2-yl)-2-methoxyethanesulfonamide (Compound 36)

(R)-N-(3-(1-(6-(5-cyclopropyl-1,2,4-oxadiasol-3-yl) pyridin-3-yl)-2,2,2-trifluoroethoxy)quinoxalin-2-yl)-2-methoxyethanesulfonamide (Compound 37)

In the same manner as in Example 28, compound 23 (440 mg) was resolved into enantiomers, compound 36 (220 mg) and compound 37 (220 mg), by preparative high performance liquid chromatography [CHIRALCEL OJ-H (Daicel Chemical Industries), particle diameter 5 μm, 2 cm (internal diameter)×25 cm (length), methanol/acetonitrile/acetic acid=95/5/0.1 (v/v), flow rate 5.7 mL/min, column oven temperature 40° C., detection wavelength 260 nm]. The compound with a retention time of 20.8 minutes was designated as compound 36 and the compound with a retention time of 32.5 minutes was designated as compound 37.
Compound 36: ESIMS m/z: 551 (M+H)$^+$.
Compound 37: ESIMS m/z: 551 (M+H)$^+$.

Next, regarding compounds 312 and 313, which are the kynurenine production inhibitors described in WO 2010/053182, the absolute configuration of each compound was determined by X-ray crystal structure analysis. From the relationship of the absolute configurations of compounds 312 and 313 to their inhibitory activities on the kynurenine production, the absolute configurations of enantiomers of compound (I) of the present application (structural analogs of compounds 312 and 313) were speculated. This experiment will be illustrated in Example 33.

Example 33

N-{3-[2,2,2-trifluoro-1-(pyridin-3-yl)ethoxy]quinoxalin-2-yl}propane-1-sulfonamide (compound 179 of Example 174 in WO 2010/053182) has a chiral carbon at the position marked with an asterisk (*) in formula B below and is a racemate of the corresponding enantiomers, compounds 312 and 313 of WO 2010/053182. In this Example, the absolute configurations of the chiral carbons of the enantiomers were determined by X-ray crystal structure analysis as described below.

[Chemical Formula 19]

Formula B

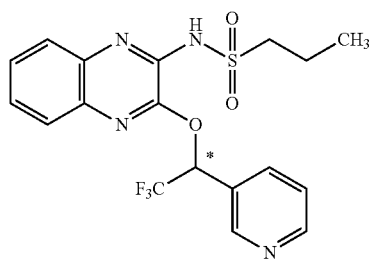

WO2010/053182 Compound 179

About 1 mg of compound 312 or compound 313 of WO 2010/053162 was weighed into a screw-top bottle and methanol was gradually added thereto to completely dissolve the compound. A screw cap was loosely screwed on so as not to prevent air flow. The screw-top bottle was left to stand in a dark place at room temperature to allow the solvent to evaporate off. Within one week after that, colorless plate crystals were obtained.

The generated crystals were cut into a maximum length of about 0.3 mm, and placed on an imaging plate (IP) X-ray diffractometer R-AXIS RAPID-IT (Rigaku Corporation). The diffraction analysis was performed using Cu Kα radiation (λ=1.5418 Å, 1 Å=10⁻¹⁰ m). Extraction of the diffraction intensity data from IP images and correction of the X-ray absorption by the crystal were performed by using software, RAPID AUTO version 2.40 (Rigaku Corporation) and CrystalStructure version 3.8.2 (Rigaku Corporation).

Crystal Structure Analysis

The initial structure was determined by using the direct method program of SHELXS-97 (Sheldrick G M. A short history of SHELX. Acta Crystallogr. Sect. A. 2008; 64 (1): 112-22.). The structure refinement by least squares method was then performed by using the structure refinement program of SHELXL-97 (Sheldrick G M. A short histry of SHELX. Acta Crystallogr. Sect. A. 2008; 64 (1): 112-22.). The absolute structure of the crystal was verified by the absolute structure parameter method (Flack H D. On enantiomorph-polarity estimation. Acta Crystallogr. Sect. A. 1983; 39 (6):876-81.). The crystal structure diagram was produced by using Mercury version 2.4.6 (Cambridge Crystallographic Data Centre).

Table 6 shows the crystal data of compound 312 and the detailed results of structural analysis. Table 7 shows the atomic coordinates and the equivalent isotropic displacement parameters (of atoms other than hydrogen atoms) or the isotropic displacement parameters (of hydrogen atoms). FIG. 1 shows the molecular structure in the crystal. For compound 312, the absolute structure parameter x resulted in −0.004 (17) and the absolute configuration of C1" in this structure was determined to be R.

Figure 2:
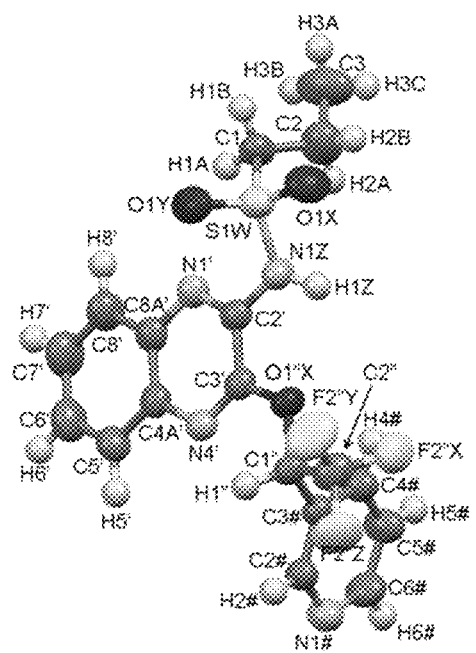
FIG. 2 shows the molecular structure of compound 313 (WO 2010/053182) in a crystal. Non-hydrogen atoms are drawn as 50% probability ellipsoids and hydrogen atoms are drawn as spheres of arbitrary radii.

Table 8 shows the crystal data of compound 313 and the detailed results of structural analysis. Table 9 shows the atomic coordinates and the equivalent isotropic displacement parameters (of atoms other than hydrogen atoms) or the isotropic displacement parameters (of hydrogen atoms). FIG. 2 shows the molecular structure in the crystal. In this crystal, when the absolute configuration of C1" in the structure was assigned to be S, the parameter x was 0.01 (2).

TABLE 6

Crystal data of compound 312 and the detailed results of structural analysis.
The values in the parentheses are the standard deviations of the last digits of the measurement values.

| Crystal data | |
|---|---|
| Molecular formula | $C_{18}H_{17}F_3N_4O_3S$ |
| Formula weight (Da) | 426.41 |
| Crystal system | Orthorhombic system |
| Space group | $P2_12_12_1$ |
| a (Å) | 7.92022(14) |
| b (Å) | 11.3514(2) |
| c (Å) | 21.9144(4) |
| V (Å³) | 1970.24(6) |
| Z | 4 |
| $\theta_{min}$ (°) | 4.03 |
| $\theta_{max}$ (°) | 68.21 |
| $R_{int}$ | 0.0590 |
| Number of measured diffraction spots/ number of theoretical diffraction spots | 1.000 |
| Structure refinement | |
| R [F² > 2σ(F²)] | 0.0324 |
| wR(F²) | 0.0817 |
| S | 1.105 |
| Number of diffraction spots for structure refinement | 3595 |
| Number of parameters | 297 |
| $\Delta\rho_{max}$ (eÅ⁻³) | 0.134 |
| $\Delta\rho_{min}$ (eÅ⁻³) | −0.235 |
| Flack's absolute structure parameter | −0.004(17) |
| Number of Friedel pairs | 1510 |

TABLE 7

The fractional coordinates of atoms and the equivalent isotropic displacement parameters ($U_{eq}$) of non-hydrogen atoms or the isotropic displacement parameters ($U_{iso}$) of hydrogen atoms in the crystal of compound 312.

| Atom | x | y | z | Ueq or Uiso (Å²) |
|---|---|---|---|---|
| C1 | −0.0331(3) | 0.8715(2) | 0.48154(10) | 0.0618(6) |
| H1A | −0.1330(19) | 0.9041(6) | 0.5012(4) | 0.091(9) |
| H1B | −0.0170(4) | 0.7920(15) | 0.4972(3) | 0.074(8) |
| C2 | 0.1164(5) | 0.9445(3) | 0.49884(14) | 0.0887(10) |
| H2A | 0.1163(5) | 1.012(2) | 0.4761(7) | 0.162(19) |
| H2B | 0.212(3) | 0.9040(13) | 0.4898(3) | 0.22(3) |
| C3 | 0.1187(5) | 0.9769(4) | 0.56506(16) | 0.1024(13) |
| H3A | 0.028(3) | 1.025(2) | 0.5736(4) | 0.135(15) |
| H3B | 0.218(3) | 1.016(2) | 0.5740(4) | 0.159(18) |
| H3C | 0.112(4) | 0.9093(16) | 0.5885(6) | 0.18(2) |
| S1W | −0.06994(7) | 0.86342(5) | 0.40261(2) | 0.05493(17) |
| O1X | −0.0709(3) | 0.97973(15) | 0.37785(7) | 0.0738(5) |
| O1Y | −0.2133(2) | 0.78988(17) | 0.39365(9) | 0.0812(6) |
| N1Z | 0.0964(2) | 0.80080(16) | 0.37182(8) | 0.0514(4) |
| H1Z | 0.155(3) | 0.845(2) | 0.3537(11) | 0.059(7) |

TABLE 7-continued

The fractional coordinates of atoms and the equivalent isotropic displacement parameters ($U_{eq}$) of non-hydrogen atoms or the isotropic displacement parameters ($U_{iso}$) of hydrogen atoms in the crystal of compound 312.

| Atom | x | y | z | Ueq or Uiso (Å²) |
|---|---|---|---|---|
| N1' | 0.0846(2) | 0.61985(15) | 0.42192(7) | 0.0493(4) |
| C2' | 0.1285(2) | 0.68045(17) | 0.37443(9) | 0.0429(4) |
| C3' | 0.2062(2) | 0.62378(17) | 0.32266(8) | 0.0412(4) |
| N4' | 0.2320(2) | 0.51226(14) | 0.31924(7) | 0.0455(4) |
| C4A' | 0.1866(2) | 0.44625(18) | 0.36953(9) | 0.0457(5) |
| C5' | 0.2161(3) | 0.32421(19) | 0.36919(12) | 0.0589(6) |
| H5' | 0.2666(17) | 0.2854(13) | 0.3327(12) | 0.095(10) |
| C6' | 0.1748(4) | 0.2594(2) | 0.41969(13) | 0.0725(7) |
| H6' | 0.1948(7) | 0.175(2) | 0.41971(13) | 0.078(8) |
| C7' | 0.1047(4) | 0.3119(2) | 0.47063(13) | 0.0786(8) |
| H7' | 0.0774(10) | 0.2640(16) | 0.5062(12) | 0.091(8) |
| C8' | 0.0729(4) | 0.4310(2) | 0.47184(11) | 0.0659(6) |
| H8' | 0.0230(14) | 0.4671(10) | 0.5076(10) | 0.060(7) |
| C8A' | 0.1138(3) | 0.49978(18) | 0.42052(9) | 0.0481(5) |
| C1" | 0.3150(3) | 0.6423(2) | 0.22226(8) | 0.0454(4) |
| H1" | 0.2407(16) | 0.5734(15) | 0.2101(3) | 0.047(6) |
| C2" | 0.3021(3) | 0.7386(2) | 0.17467(10) | 0.0613(6) |
| O1"X | 0.24898(17) | 0.69666(12) | 0.27618(6) | 0.0469(3) |
| F2"X | 0.3990(2) | 0.83080(12) | 0.18757(7) | 0.0742(4) |
| F2"Y | 0.1463(2) | 0.77751(17) | 0.16842(8) | 0.0975(5) |
| F2"Z | 0.3528(2) | 0.69715(15) | 0.12058(6) | 0.0868(5) |
| N1# | 0.7156(2) | 0.47231(16) | 0.19565(9) | 0.0576(5) |
| C2# | 0.5563(2) | 0.51095(18) | 0.19356(9) | 0.0499(5) |
| H2# | 0.484(2) | 0.4756(10) | 0.1666(7) | 0.054(6) |
| C3# | 0.4947(2) | 0.60101(17) | 0.22968(8) | 0.0422(4) |
| C4# | 0.6041(3) | 0.6525(2) | 0.27076(10) | 0.0517(5) |
| H4# | 0.5672(10) | 0.7140(15) | 0.2964(6) | 0.054(6) |
| C5# | 0.7678(3) | 0.6125(2) | 0.27376(11) | 0.0633(6) |
| H5# | 0.843(2) | 0.6452(10) | 0.3013(8) | 0.077(8) |
| C6# | 0.8181(3) | 0.5234(2) | 0.23543(11) | 0.0622(6) |
| H6# | 0.928(4) | 0.4980(9) | 0.23749(13) | 0.098(10) |

The initial letters "C", "H", "S", "O", "N" and "F" of the atoms represent carbon, hydrogen, sulfur, oxygen, nitrogen and fluorine, respectively.

TABLE 8

Crystal data of compound 313 and the detailed results of structural analysis. The values in the parentheses are the standard deviations of the last digits of the measurement values.

| Crystal data | |
|---|---|
| Molecular formula | $C_{18}H_{17}F_3N_4O_3S$ |
| Formula weight (Da) | 426.41 |
| Crystal system | Orthorhombic system |
| Space group | $P2_12_12_1$ |
| a (Å) | 7.91887(14) |
| b (Å) | 11.3519(2) |
| c (Å) | 21.9152(4) |
| V (ų) | 1970.05(6) |
| Z | 4 |
| $R_{int}$ | 0.0302 |
| Number of measured diffraction spots/ number of theoretical diffraction spots | 0.963 |
| Structure refinement | |
| R [F² > 2σ(F²)] | 0.0359 |
| wR(F²) | 0.0898 |
| S | 1.100 |
| Number of diffraction spots for structure refinement | 3452 |
| Number of parameters | 298 |
| Δρ$_{max}$ (eÅ⁻³) | 0.236 |
| Δρ$_{min}$ (eÅ⁻³) | −0.200 |
| Flack's absolute structure parameter | 0.01(2) |
| Number of Friedel pairs | 1445 |

TABLE 9

The fractional coordinates of atoms and the equivalent isotropic displacement parameters ($U_{eq}$) of non-hydrogen atoms or the isotropic displacement parameters ($U_{iso}$) of hydrogen atoms in the crystal of compound 313.

| Atom | x | y | z | Ueq or Uiso (Å²) |
|---|---|---|---|---|
| C1 | 1.0330(5) | 0.1285(3) | 0.51834(13) | 0.0663(9) |
| H1A | 1.0163(6) | 0.2080(19) | 0.5026(4) | 0.078(11) |
| H1B | 1.133(2) | 0.0961(8) | 0.4986(5) | 0.108(14) |
| C2 | 0.8840(7) | 0.0550(5) | 0.50144(18) | 0.0950(15) |
| H2A | 0.789(4) | 0.0946(17) | 0.5107(4) | 0.23(4) |
| H2B | 0.8852(7) | −0.012(3) | 0.5237(10) | 0.21(3) |
| C3 | 0.8820(7) | 0.0235(6) | 0.4345(2) | 0.1089(18) |
| H3A | 0.976(4) | −0.023(3) | 0.4255(5) | 0.17(3) |
| H3B | 0.886(5) | 0.092(2) | 0.4112(7) | 0.22(4) |
| H3C | 0.783(4) | −0.018(3) | 0.4255(5) | 0.15(2) |
| S1W | 1.06971(11) | 0.13662(7) | 0.59737(3) | 0.0607(2) |
| O1X | 1.0707(4) | 0.02015(18) | 0.62226(10) | 0.0779(7) |
| O1Y | 1.2128(3) | 0.2103(2) | 0.60640(11) | 0.0855(8) |
| N1Z | 0.9036(4) | 0.1988(2) | 0.62816(11) | 0.0550(7) |
| H1Z | 0.838(5) | 0.150(3) | 0.6486(15) | 0.084(12) |
| N1' | 0.9153(3) | 0.3805(2) | 0.57798(10) | 0.0534(6) |
| C2' | 0.8713(4) | 0.3197(2) | 0.62570(12) | 0.0480(7) |
| C3' | 0.7941(4) | 0.3764(2) | 0.67739(11) | 0.0461(6) |
| N4' | 0.7674(3) | 0.48809(19) | 0.68079(10) | 0.0491(6) |
| C4A' | 0.8136(4) | 0.5538(2) | 0.63041(13) | 0.0498(7) |
| C5' | 0.7841(5) | 0.6760(2) | 0.63089(16) | 0.0629(9) |
| H5' | 0.7319(19) | 0.7164(15) | 0.6690(14) | 0.091(12) |
| C6' | 0.8251(5) | 0.7408(3) | 0.58038(17) | 0.0780(11) |
| H6' | 0.8039(9) | 0.826(3) | 0.58020(17) | 0.091(12) |
| C7' | 0.8960(6) | 0.6879(3) | 0.52946(18) | 0.0841(13) |
| H7' | 0.9237(13) | 0.735(2) | 0.4948(15) | 0.094(12) |
| C8' | 0.9269(5) | 0.5691(3) | 0.52827(15) | 0.0710(10) |
| H8' | 0.9778(18) | 0.5319(13) | 0.4915(12) | 0.069(10) |
| C8A' | 0.8861(4) | 0.5005(2) | 0.57952(12) | 0.0523(7) |
| C1" | 0.6848(4) | 0.3578(3) | 0.77772(11) | 0.0484(7) |
| H1" | 0.759(2) | 0.427(2) | 0.7898(4) | 0.055(8) |
| C2" | 0.6984(5) | 0.2620(3) | 0.82512(14) | 0.0657(9) |
| O1"X | 0.7510(3) | 0.30330(16) | 0.72382(8) | 0.0514(5) |
| F2"X | 0.6010(3) | 0.16944(16) | 0.81249(9) | 0.0796(6) |
| F2"Y | 0.8532(3) | 0.2225(2) | 0.83156(10) | 0.1021(8) |
| F2"Z | 0.6472(3) | 0.3031(2) | 0.87942(8) | 0.0916(7) |
| N1# | 0.2853(4) | 0.5281(2) | 0.80453(12) | 0.0622(7) |
| C2# | 0.4439(5) | 0.4892(2) | 0.80641(13) | 0.0531(7) |
| H2# | 0.516(3) | 0.5242(12) | 0.8332(9) | 0.061(10) |
| C3# | 0.5053(4) | 0.3993(2) | 0.77021(12) | 0.0460(7) |
| C4# | 0.3958(4) | 0.3475(3) | 0.72936(13) | 0.0576(8) |
| H4# | 0.4324(13) | 0.286(2) | 0.7041(9) | 0.074(10) |
| C5# | 0.2327(5) | 0.3873(3) | 0.72619(15) | 0.0680(9) |
| H5# | 0.154(3) | 0.3532(13) | 0.6975(11) | 0.092(12) |
| C6# | 0.1832(5) | 0.4770(3) | 0.76475(15) | 0.0690(9) |
| H6# | 0.075(5) | 0.5023(12) | 0.76272(17) | 0.087(12) |

The initial letters "C", "H", "S", "O", "N" and "F" of the atoms represent carbon, hydrogen, sulfur, oxygen, nitrogen and fluorine, respectively.

From the above results, the absolute configurations of the chiral carbons of the compounds of WO 2010/053182 were determined to be R for compound 312 and S for compound 313.

[Chemical Formula 20]

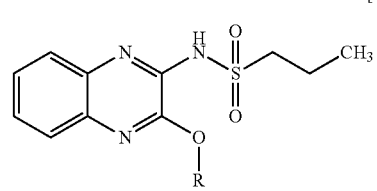

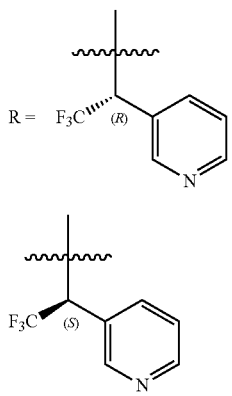

Compound 312

Compound 313

The inhibitory activities on the kynurenine production of compounds 312 and 313 were determined by the measurement method in Test Example 1 to be $IC_{60}=39$ nmol/L and 9900 nmol/L, respectively. Compound 312 showed stronger inhibitory activity.

Based on the above results, the configurations of two enantiomers of compound (I) of the present application, which are structural analogs of the above compounds 312 and 313, was speculated for the case where, around the chiral carbon marked with the asterisk (*), $R^2$ is on the lower right side, $R^3$ is on the lower left side and the 3-substituted quinoxalin-2-yloxy group is on the upper side, as shown in the following formula (I):

[Chemical Formula 21]

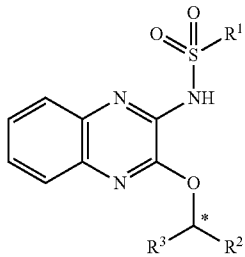

(I)

(wherein $R^1$, $R^2$ and $R^3$ each have the same meanings as defined above). First, the inhibitory activity on the kynurenine production was measured for the enantiomers of compound (I) of the present application. Then, the configurations of $R^2$, $R^3$ and the 3-substituted quinoxalin-2-yloxy group around the chiral carbon (*) in formula (I) was speculated as follows: the enantiomer with a stronger inhibitory activity on the kynurenine production has the same configuration as that of compound 312, whereas the enantiomer with a weaker inhibitory activity on the kynurenine production has the same configuration as that of compound 313.

Preparation Example 1

Tablets having the following composition are prepared in a usual manner. Compound 21 (40 g) is mixed with lactose (286.8 g) and potato starch (60 g). To the mixture is added a 10% aqueous hydroxypropyl cellulose solution (120 g). The mixture is kneaded, granulated, dried, and fine-granulated in a usual manner to prepare granules for tableting. To the mixture is added magnesium stearate (1.2 g) and the mixture is mixed. The mixture is tableted with a tableting machine (Kikusui, Model RT-15) equipped with a pestle whose diameter is 8 mm to give tablets (each containing 20 mg of the active ingredient).

TABLE 10

| Formula | Compound 21 | 20 mg |
|---|---|---|
| | Lactose | 143.4 mg |
| | Potato starch | 30 mg |
| | Hydroxypropyl cellulose | 6 mg |
| | Magnesium stearate | 0.6 mg |
| | | 200 mg |

Preparation Example 2

Capsules having the following composition are prepared in a usual manner. Compound 21 (200 g) is mixed with Avicel (995 g) and magnesium stearate (5 g) in a usual manner. The mixture is filled into hard capsules (#4) (volume: 120 mg per capsule) with a capsule filling machine (Zanasi, Model LZ-64) to give capsules (each containing 20 mg of the active ingredient).

TABLE 11

| Formula | Compound 21 | 20 mg |
|---|---|---|
| | Avicel | 99.5 mg |
| | Magnesium stearate | 0.5 mg |
| | | 120 mg |

Preparation Example 3

An injection having the following composition is prepared in a usual manner. Compound 25 (1 g) and D-mannitol (5 g) are added to distilled water for injection and mixed. The pH is adjusted to 6 by adding hydrochloric acid and an aqueous sodium hydroxide solution, and the total volume is made up to 1000 mL with distilled water for injection. Two mL of the mixture is aseptically filled into each glass vial, and thus an injection (containing 2 mg of the active ingredient per vial) is obtained.

TABLE 12

| Formula | Compound 25 | 2 mg |
|---|---|---|
| | D-mannitol | 10 mg |
| | Hydrochloric acid | q.s. |
| | Aqueous sodium hydroxide solution | q.s. |
| | Distilled water for injection | q.s. |
| | | 2.00 mL |

INDUSTRIAL APPLICABILITY

The present invention provides a nitrogen-containing heterocyclic compound having an inhibitory effect on the production of kynurenine or a pharmaceutically acceptable salt thereof; a kynurenine production inhibitor comprising one or more of said compounds and/or salts thereof as an active ingredient; and the like.

The invention claimed is:

1. A nitrogen-containing heterocyclic compound selected from the group consisting of:
- N,N-dimethyl-2-(4-(2,2,2-trifluoro-1-(3-(propylsulfonamido)quinoxalin-2-yloxy)ethyl)piperidin-1-yl)isonicotinamide (compound 1),
- N,N-dimethyl-2-(4-(2,2,2-trifluoro-1-(3-(propylsulfonamido)quinoxalin-2-yloxy)ethyl)piperidin-1-yl)nicotinamide (compound 2),
- N,N-dimethyl-6-(4-(2,2,2-trifluoro-1-(3-(propylsulfonamido)quinoxalin-2-yloxy)ethyl)piperidin-1-yl)picolinamide (compound 3),
- N-(3-(1-(1-(6-cyanopyridin-3-yl)piperidin-4-yl)-2,2,2-trifluoroethoxy)quinoxalin-2-yl)propane-1-sulfonamide (compound 4),
- 5-(4-(2,2,2-trifluoro-1-(3-(propylsulfonamido)quinoxalin-2-yloxy)ethyl)piperidin-1-yl)picolinamide (compound 5),
- N-(3-(1-(1-(4-cyanopyridin-2-yl)piperidin-4-yl)-2,2,2-trifluoroethoxy)quinoxalin-2-yl)propane-1-sulfonamide (compound 6),
- N-(3-(1-(1-(5-cyanopyridin-3-yl)piperidin-4-yl)-2,2,2-trifluoroethoxy)quinoxalin-2-yl)propane-1-sulfonamide (compound 7),
- N,N-dimethyl-6-(4-(2,2,2-trifluoro-1-(3-(propylsulfonamido)quinoxalin-2-yloxy)ethyl)piperidin-1-yl)nicotinamide (compound 8),
- N-(3-(1-(1-(3-cyanopyridin-2-yl)piperidin-4-yl)-2,2,2-trifluoroethoxy)quinoxalin-2-yl)propane-1-sulfonamide (compound 9),
- 2-(4-(2,2,2-trifluoro-1-(3-(propylsulfonamido)quinoxalin-2-yloxy)ethyl)piperidin-1-yl)nicotinamide (compound 10),
- N-(3-(2,2,2-trifluoro-1-(1-(2-methyl-2H-tetrazol-5-yl)piperidin-4-yl)ethoxy)quinoxalin-2-yl)propane-1-sulfonamide (compound 11),
- N-(3-(2,2,2-trifluoro-1-(1-(1-methyl-1H-tetrazol-5-yl)piperidin-4-yl)ethoxy)quinoxalin-2-yl)propane-1-sulfonamide (compound 12),
- N-(3-(2,2,2-trifluoro-1-(1-(pyrazin-2-yl)piperidin-4-yl)ethoxy)quinoxalin-2-yl)propane-1-sulfonamide (compound 13),
- N-(3-(2,2,2-trifluoro-1-(1-(pyrimidin-5-yl)piperidin-4-yl)ethoxy)quinoxalin-2-yl)propane-1-sulfonamide (compound 14),
- N-(3-(1-(1-(5-cyanopyridin-2-yl)piperidin-4-yl)-2,2,2-trifluoroethoxy)quinoxalin-2-yl)propane-1-sulfonamide (compound 15),
- N-(3-(1-(1-(2-cyanopyridin-4-yl)piperidin-4-yl)-2,2,2-trifluoroethoxy)quinoxalin-2-yl)propane-1-sulfonamide (compound 16),
- N-(3-(1-(1-(3-cyanopyridin-4-yl)piperidin-4-yl)-2,2,2-trifluoroethoxy)quinoxalin-2-yl)propane-1-sulfonamide (compound 17),
- N-(3-(2,2,2-trifluoro-1-(1-(thiazol-2-yl)piperidin-4-yl)ethoxy)quinoxalin-2-yl)propane-1-sulfonamide (compound 18),
- 6-(4-(2,2,2-trifluoro-1-(3-(propylsulfonamido)quinoxalin-2-yloxy)ethyl)piperidin-1-yl)nicotinamide (compound 19),
- N-(3-(2,2,2-trifluoro-1-(1-(pyridin-2-yl)piperidin-4-yl)ethoxy)quinoxalin-2-yl)propane-1-sulfonamide (compound 20),
- N-(3-(2,2,2-trifluoro-1-(1-(pyridin-3-yl)piperidin-4-yl)ethoxy)quinoxalin-2-yl)propane-1-sulfonamide (compound 21), and
- N-(3-(2,2,2-trifluoro-1-(1-(pyridin-4-yl)piperidin-4-yl)ethoxy)quinoxalin-2-yl)propane-1-sulfonamide (compound 22); or a pharmaceutically acceptable salt thereof.

2. A nitrogen-containing heterocyclic compound selected from the group consisting of:
- N-(3-(1-(6-(5-cyclopropyl-1,2,4-oxadiazol-3-yl)pyridin-3-yl)-2,2,2-trifluoroethoxy)quinoxalin-2-yl)-2-methoxyethanesulfonamide (compound 23),
- 2-methoxy-N-(3-(2,2,2-trifluoro-1-(6-(5-(methoxymethyl)-1,2,4-oxadiazol-3-yl)pyridin-3-yl)ethoxy)quinoxalin-2-yl)ethanesulfonamide (compound 24),
- N-(3-(1-(6-(5-cyclopropyl-1,2,4-oxadiazol-3-yl)pyridin-3-yl)-2,2,2-trifluoroethoxy)quinoxalin-2-yl)propane-1-sulfonamide (compound 25),
- N-(3-(2,2,2-trifluoro-1-(6-(5-(methoxymethyl)-1,2,4-oxadiazol-3-yl)pyridin-3-yl)ethoxy)quinoxalin-2-yl)propane-1-sulfonamide (compound 26), and
- 2-methoxy-N-(3-(2,2,2-trifluoro-1-(6-(5-methyl-1,2,4-oxadiazol-3-yl)pyridin-3-yl)ethoxy)quinoxalin-2-yl)ethanesulfonamide (compound 27); or a pharmaceutically acceptable salt thereof.

3. A nitrogen-containing heterocyclic compound selected from the group consisting of:
- (R)-N-(3-(2,2,2-trifluoro-1-(6-(5-methyl-1,2,4-oxadiazol-3-yl)pyridin-3-yl)ethoxy)quinoxalin-2-yl)propane-1-sulfonamide (compound 28),
- (R)-2-methoxy-N-(3-(2,2,2-trifluoro-1-(6-(oxazol-5-yl)pyridin-3-yl)ethoxy)quinoxalin-2-yl)ethanesulfonamide (compound 30),
- (S)-N-(3-(1-(2-acetylthiazol-5-yl)-2,2,2-trifluoroethoxy)quinoxalin-2-yl)propane-1-sulfonamide (compound 32),
- (R)-5-(4-(2,2,2-trifluoro-1-(3-(propylsulfonamido)quinoxalin-2-yloxy)ethyl)piperidin-1-yl)picolinamide (compound 34), and
- (R)-N-(3-(1-(6-(5-cyclopropyl-1,2,4-oxadiazol-3-yl)pyridin-3-yl)-2,2,2-trifluoroethoxy)quinoxalin-2-yl)-2-methoxyethanesulfonamide (compound 37); or a pharmaceutically acceptable salt thereof.

4. A nitrogen-containing heterocyclic compound selected from the group consisting of:
- (S)-N-(3-(2,2,2-trifluoro-1-(6-(5-methyl-1,2,4-oxadiazol-3-yl)pyridin-3-yl)ethoxy)quinoxalin-2-yl)propane-1-sulfonamide (compound 29),
- (S)-2-methoxy-N-(3-(2,2,2-trifluoro-1-(6-(oxazol-5-yl)pyridin-3-yl)ethoxy)quinoxalin-2-yl)ethanesulfonamide (compound 31),
- (R)-N-(3-(1-(2-acetylthiazol-5-yl)-2,2,2-trifluoroethoxy)quinoxalin-2-yl)propane-1-sulfonamide (compound 33),
- (S)-5-(4-(2,2,2-trifluoro-1-(3-(propylsulfonamido)quinoxalin-2-yloxy)ethyl)piperidin-1-yl)picolinamide (compound 35), and
- (S)-N-(3-(1-(6-(5-cyclopropyl-1,2,4-oxadiazol-3-yl)pyridin-3-yl)-2,2,2-trifluoroethoxy)quinoxalin-2-yl)-2-methoxyethanesulfonamide (compound 36); or a pharmaceutically acceptable salt thereof.

* * * * *